(12) United States Patent
Billeter et al.

(10) Patent No.: US 7,402,429 B1
(45) Date of Patent: Jul. 22, 2008

(54) HOST CELLS COMPRISING CDNA CORRESPONDING TO THE ANTIGENOME OF NONSEGMENTED NEGATIVE STRAND RNA VIRUSES, FURTHER ENCODING ANTIGENICALLY ACTIVE PROTEINS

(75) Inventors: Martin A. Billeter, Zurich (CH); Pius Spielhofer, Zurich (CH); Karin Kälin, Gif-sur-Yvette (FR); Frank Radecke, Zurich (CH); Henriette Schneider, Zurich (CH)

(73) Assignee: Schweiz Serum & Impfinstitut Bern (CH)

( * ) Notice: Subject to any disclaimer, the term of this patent is extended or adjusted under 35 U.S.C. 154(b) by 0 days.

(21) Appl. No.: 09/011,425

(22) PCT Filed: Aug. 9, 1996

(86) PCT No.: PCT/EP96/03544

§ 371 (c)(1),
(2), (4) Date: Sep. 15, 1998

(87) PCT Pub. No.: WO97/06270

PCT Pub. Date: Feb. 20, 1997

(30) Foreign Application Priority Data

Aug. 9, 1995  (EP) ................................. 95112559

(51) Int. Cl.
| | | |
|---|---|---|
| *A01N 63/00* | (2006.01) | |
| *A01N 65/00* | (2006.01) | |
| *A61K 48/00* | (2006.01) | |
| *C12N 5/00* | (2006.01) | |
| *C12N 5/02* | (2006.01) | |
| *C12N 15/00* | (2006.01) | |

(52) U.S. Cl. .................. 435/325; 435/320.1; 424/93.1; 424/93.2

(58) Field of Classification Search ............... 435/235, 435/325, 320.1; 536/23.1, 23.5; 424/93.2, 424/9.1, 93.1, 93.6
See application file for complete search history.

(56) References Cited

U.S. PATENT DOCUMENTS

| | | | |
|---|---|---|---|
| 5,166,057 A | 11/1992 | Palese et al. ............... 435/69.1 |
| 5,240,703 A | 8/1993 | Cochran .................. 424/205.1 |
| 5,840,520 A * | 11/1998 | Clarke et al. ............... 435/69.1 |
| 6,033,886 A * | 3/2000 | Conzelmann ............ 424/205.1 |

FOREIGN PATENT DOCUMENTS

| | | |
|---|---|---|
| CA | 2035386 | 1/1991 |
| CA | 2065245 | 3/1991 |
| CA | 2154023 | 4/2007 |
| EP | A 0440219 | 8/1991 |
| EP | 0702085 A1 | 3/1996 |
| EP | A 0 702 085 | 3/1996 |
| WO | WO 95/03070 | 2/1995 |
| WO | WO 96/34625 | 11/1996 |

OTHER PUBLICATIONS

Verma et al. Gene Therapy-Promises, Problems, and Prospects. Nature, vol. 389, pp. 239-242, Sep. 18, 1997.*
Eck et al. Gene-Based Therapy. Goodman & Gilman's The Pharmacological Basis of Therapeutics, 9th Edition, Chapter 5, 1996.*
Calain et al. (1993) The rule of six, a basic feature for efficient replication of Sendai virus defective interfering RNA. J. Virol. 67: 4822-4830.*
Kolakofsky et al. (1998) Paramyxovirus RNA synthesis and the requirement for hexamer genome length: the rule of six revisited. J. Virol. 72(2): 891-899.*
Tordo et al. (1992) Evolution of negative-stranded RNA genomes. Seminars in Virology 3: 341-357.*
Dorland's Illustrated Medical Dictionary (30th Edition, 2003) Philadelphia: W.B. Saunders and Company, pp. 565 and 1414.*
Takeda et al. (2000) Recovery of pathogenic measles virus from cloned cDNA. J. Virol. 74(14): 6643-6647.*
Sidhu M.S. et al., "Rescue of synthetic measles virus minireplicons: measles genomic termini direct efficient expression and propagation of a reporter gene", Apr. 20, 1995, *Virology*, 208(2): 800-807.
Ballart I et al., "Infectious measles virus from cloned cDNA", 1990, Eur *Mol Biol Organ [EMBO]J*, 9(2):379-384 [retracting by Eschle D., et al. (1991) EMBO J, 10(11):3558.
Ballart I et al Retraction of BA 89092782. Infectious Measles Virus from Cloned Complementary DNA. Retracted by Authors Daniel Eschle, et al., (1991) EMBO J, 10(11):3558.
Calain P. et al., "The rule of six, a basic feature for efficient replication of sendai virus defective interfering RNA", (1993) *J of Virology*, 67(8):4822-4830.
Willenbrink et al. "Long-term replication of sendai virus defective interfering particle nucleocapsids in stable helper cell lines", (1994) *J of Virology*, 68(12):8413-8417.
Wertz G. et al., "Extent of terminal complementarity modulates the balance between transcription and replication of vesicular stomatitis virus RNA" (1994) *Proceedings of the Nat'l Ac. Of Sciences of USA*. 91:19:8587-8591.
Schnell M. J. et al., "Infectious rabies viruses from cloned cDNA", (1994) *EMBO J*, 13(18):4195-4203.
Lawson N.D. et al., "Recombinant vesicular stomatitis viruses from DNA" (1995) *Proceedings of the National Academy of Sciences of USA*, 92(9):4477-4481.
Whelan S.P. et al., "Efficient Recovery of Infectious Vesicular Stomatitis Virus Entirely from cDNA Clones" (1995) *Proc Natl Acad Sci USA*. 92(18):8388-8392.

(Continued)

*Primary Examiner*—Anne-Marie Falk
(74) *Attorney, Agent, or Firm*—McDonnell Boehnen Hulbert & Berghoff LLP

(57) ABSTRACT

The present invention relates, in general, to a methodology for the generation or nonsegmented negative-strand RNA viruses (Pringle, 1991) from cloned deoxyribonucleic acid (cDNA). Such rescued viruses are suitable for use as vaccines, or alternatively, as plasmids in somatic gene therapy applications. The invention also relates to cDNA molecules suitable as tools in this methodology and to helper cell lines allowing the direct rescue of such viruses. Measles virus (MV) is used as a model for other representatives of the Mononegavirales, in particular the family Paramyxoviridae.

20 Claims, 12 Drawing Sheets

OTHER PUBLICATIONS

Figure 1:
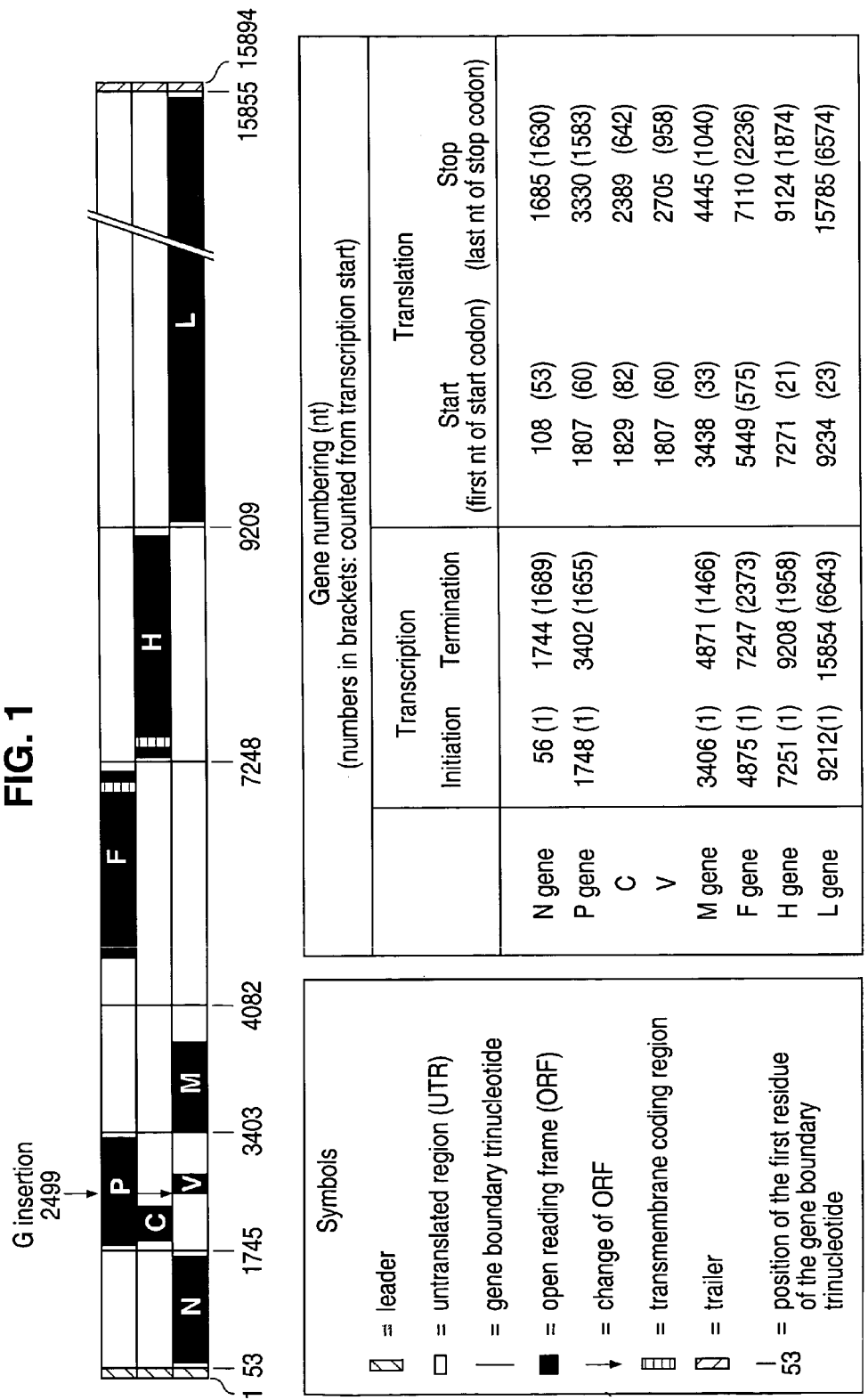

Radecke F. et al., "Rescue of measles viruses from cloned DNA" (1995) *EMBO J*, 14(23):5773-5784.

Karin Kalin, "Requirements for Amplification of Synthetic Measles Virus and Canine Distemper Virus Subgenomic RNAs", Inaugural-Dissertation, Zurich 1995.

Calain, P., et al., Molecular cloning of natural paramyxovirus copy-black defective interfering RNAs and their expression from DNA, *Virology*, 191:62-71 (1992).

Engelhorn, M., et al., Molecular cloning and characterization of a Sendai virus internal delection defective RNA, *Journal of General Virology*, 74:137-141 (1993).

Enami, M., et al., A measles virus subgenomic RNA: Structure and generation mechanism, *Virology* 171:427-433 (1989).

Harty, R.N., et al., Mutations within noncoding terminal sequences of model RNAs of Sendai virus: Influence on reporter gene expression, *Journal of Virology*, 69(8):5128-5131 (1995).

Sidhu, M.S., et al., Defective measles virus in human subacute sclerosing panencephalitis brain, *Virology*, 202:631-641 (1994).

Collins, et al., "Production of infectious human respiratory syncytial virus from cloned cDNA confirms an essential role for the transcription elongation factor from the 5' proximal open reading frame of the M2 mRNA in gene expression and provides a capability for vaccine development," (Dec. 1995) *Proc. Natl. Acad. Sci.*, vol. 92, pp. 11563-11567.

Deng, et al., "High-efficiency protein synthesis from T7 RNA polymerase transcripts in 3T3 fibroblasts," (1991), *Gene*, vol. 109, pp. 193-201.

Garcin, et al., "A highly recombinogenic system for the recovery of infectious Sendai paramyxovirus from cDNA: generation of a novel copy-back nondefective interfering virus," *EMBO*, (1995) vol. 14, No. 24, pp. 6087-6094.

Lieber, et al., "High level gene expression in mammalian cells by a nuclear T7-phage RNA polymerase," *Nucleic Acids Research*, (1989), vol. 17, No. 21, pp. 8485-8493.

Elroy-Stein, et al., "Cytoplasmic expression system based on constitutive synthesis of bacteriophage T7 RNA polymerase in mammalian cells," *Proc. Natl. Acad. Sci.*, (Sep. 1990), vol. 87, pp. 6743-6747.

Whelan, et al., "Efficient recovery of infectious vesicular stomatitis virus entirely from cDNA clones," *Proc. Natl. Acad. Sci.*, (Aug. 1995), vol. 92, pp. 8388-8392.

Whetter, et al., "Analysis of hepatitis A virus translation in a T7 polymerase-expressing cell line," *Arch Virol.* (1994, Supp.), vol. 9, pp. 291-298.

Willenbrink, et al. "Long-Term Replication of Sendai Virus Defective Interfering Particle Nucleocapsids in Stable Helper Cell Lines," *Jour. Of Virol.* (Dec. 1994), vol. 68, No. 12, pp. 8413-8417.

Wyatt, et al., Replication-Deficient Vaccinia Virus Encoding Bacteriophage T7 RNA Polymerase for Transient Gene Expression in Mammalian Cells, *Virology*, (1995), vol. 210, pp. 202-205.

Baltimore et al., "Ribonucleic Acid Synthesis of Vesicular Stomatitis Virus, II. An RNA Polymerase in the Virion", 1970, Proc. Natl. Acd. Sci. 66(2):572-576.

Bricker et al., "Monoclonal Antibodies to the Glycoprotein of Vesicular Stomatitis Virus (New Jersey Serotype): A Method for Preliminary Mapping of Epitopes", 1987, Virology 161:533-540.

Collins et al., "Rescure of a 7502-Nucleotide (49.3% of Full-Length) Synthetic Analog of Respiratory Syncytial Virus Genomic RNA", 1993, Virology 195: 252-256.

Collins et al., "Rescure of synthetic analogs of respiratory syncytial virus genomic RNA and effect of truncations and mutations on the expression of a foreign reporter gene", 1991, Proc. Natl. Acad. Sci. 88:9663-9667.

Conzelmann et al., "Rescure of Synthetic Genomic RNA Analogs of Rabies Virus by Plasmid-Encoded Proteins", 1994, J. Virol. 68(2):713-719.

De et al., "Rescure of Synthetic Analogs of Genome RNA of Human Parainfluenza Virus Type 3", 1993, Virology 196:344-348.

Dimock et al., "Rescue of Synthetic Analogs of Genomic RNA and Replicative-Intermediate RNA of Human Parainfluenza Virus Type 3", 1993, J. Virol. 67(5):2772-2778.

Enami et al., "Introduction of site-specific mutations into the genome of influenza virus", 1990, Proc. Natl. Acd. Sci. 87:3802-3805.

Fuerst et al., "Eukaryotic transient-expression system based on recombinant vaccinia virus that synthesizes bacteriophage T7 RNA polymerase", 1986, Proc. Natl. Acad. Sci. 83:8122-8126.

Gallione et al., "Nucleotide Sequence of a cDNA Clone Encoding the Entire Glycoprotein from the New Jersey Serotype of Vesicular Stomatitis Virus", 1983, J. Virol. 46(1):162-169.

Gallione et al., "Nucleotide Sequences of the mRNA's Encoding the Vesicular Stomatitis Virus N and NS Proteins", 1981, J. Virol. 39(2):529-535.

Kurath et al., "Molecular Cloning of the Six mRNA Species of Infectious Hematopoietic Necrosis Virus, a Fish Rhabdovirus, and Gene Order Determination by R-Loop Mapping", 1985, J. Virol. 53(2):469-476.

Lefrancois et al., "The Interaction of Antibody with the Major Surface Glycoprotein of Vesicular Stomatitis Virus, II. Monoclonal Antibodies to Nonneutralizing and Cross-Reactive Epitopes of Indiana and New Jersey Serotypes", 1982, Virology 121:168-174.

Luytjes et al., "Amplification, Expression, and Packaging of a Foreign Gene by Influenza Virus", 1989, Cell 59:1107-1113.

Mierendorf et al,. "Sequencing of RNA Transcripts Synthesized in Vitro from Plasmids Containing Bacteriophage Promoters", 1987, Meth. Enzymol. 152:563-566.

Mullis et al., "Specific Synthesis of DNA in Vitro via a Polymerase-Catalyzed Chain Reaction", 1987, Meth. Enzymol. 155:335-350.

Owens et al., "Cytoplasmic Domain Requirement for Incorporation of a Foreign Envelope Protein into Vesicular Stomatitis Virus", 1993, J. Virol. 67(1):360-365.

Park et al., "Rescue of a foreign gene by Sendai virus", 1991, Proc. Natl. Acad. Sci. 88:5537-5541.

Pattnaik et al., "Infectious Defective Interfering Particles of VSV from Transcripts of a cDNA Clone", 1992, Cell 69:1011-1020.

Perotta et al., "A pseudoknot-like structure required for efficient self-cleavage of hepatitis delta virus RNA", 1991, Nature 350: 434-436.

Rose et al., "Nucleotide Sequences of the mRNA's Encoding the Vesicular Stomatitis Virus G and M Proteins Determined from cDNA Clones Containing the Complete Coding Regions", 1981, J. Virol. 39(2): 519-528.

Rose et al., 1987, "Rhabdovirus Genomes and Their Products", in *The Viruses: The Rhabdoviruses*, Plenum Press, New York, NY, pp. 129-166.

Schubert et al., "Expression of a cDNA encoding a functional 241-kilodalton vesicular stomatitis virus RNA polymerase", 1985, Proc. Natl. Acad. Sci. 82:7984-7988.

Seong, "Influencing the Influenza Virus: Genetic Analysis and Engineering of the Negative-Sense RNA Genome", 1993, Infect. Agents & Disease 2:17-24.

Thomas et al,. "Mass and Molecular Composition of Vesicular Stomatitis Virus: a Scanning Transmission Electron Microscopy Analysis", J. Virol. 54(2):598-607.

Tordo et al., "Walking along the rabies genome: Is the large G-L intergenic region a remnant gene?", 1986, Prov. Natl. Acd. Sci. 83:3914-3918.

Whitt et al., "Glycoprotein Cytoplasmic Domain Sequences Required for Rescue of a Vesicular Stomatitis Virus Glycoprotein Mutant", 1989, J. Virol. 63(9):3569-3578.

Das, et al., "Improved technique for transient expression and negative strand virus rescue using fowlpox T7 recombinant virus in mammalian cells", J. Virol. Methods vol. 89, pp. 119-127 (2000).

Deng, et al, "High-efficiency protein synthesis from T7 RNA polymerase transcripts in 3T3 fibroblasts", Gene vol. 109, pp. 193-201(1991).

Ballart, et al., "Infectious measles virus from cloned cDNA", EMBO J. 1991, 10(11), p. 2558 (1991).

Garcin, et al, "A highly recombinogenic system for the recovery of infectious Sendai paramyxovirus from cDNA: generation of a novel copy-back nondefective interfering virus", EMBO vol. 14, pp. 6087-6094 (1995).

He, et al., "Recovery of Infectious SV5 from Cloned DNA and Expression of a Foreign Gene", Virology vol. 237, pp. 249-260 (1997).

Kato, et al., "Initiation of Sendai virus multiplication from transfected cDNA or RNA with negative or positive sense", Genes to Cells 1:569-579 (1996).

Lieber, et al., "High level gene expression in mammalian cells by a nuclear T7-phage RNA polymerase", Nucleic Acid Res. 17, pp. 8485-9493 (1989).

McNally, et al., "Optimizing Electroporation Parameters for a Variety of Human hematopoietic Cell Lines", Biotechniques 6(9):882-886 (1988).

Mink, et al., "Nucleotide Sequences of the 3' Leader and 5' Trailer Regions of Human Respiratory Syncytial Virus Genomic RNA", Virology 185:615-624 (1991).

Ninth Int'l conference on Negative Strand Viruses (Oct. 2-7, 1994).

Schneider, et al., "Rescue of measles virus using a replication-deficient vaccinia-T7 vector", J. Virol, Methods, vol. 64, pp. 57-64 (1997).

Sidhu et al., "Canine Distemper Terminal and Intergenic Non-protein Coding Nucleotide Sequences: Completion of the Entire CDV Genome Sequence", Virology vol. 193, pp. 66-72 (1993).

Whetter, et al., Analysis of hepatitis A virus translation in a T7 polymerase-expressing cell line, Arch. V. vol. {Suppl} 9, pp. 291-298 (1994).

Wyatt, et al., "Replication-Deficient Vaccinia Virus Encoding Bacteriophage T7 RNA Polymerase for Transient Gene Expression in Mammalian Cells", Virology 210, pp. 202-205 (1995).

Lawson, et al., "Recombinant vesicular stomatitis viruses from DNA", Proc. Natl. Acad. Sci., vol. 92, pp. 4477-4481(1995).

Collins, et al., "Production of infectious human respiratory syncytial virus from cloned cDNA confirms an essential role for the transcription elongation factor from the 5' proximal open reading . . . ", Proc. Natl., Accad. Sci., vol. 92, pp. 11563-11567(1995).

Peeters, et al., "Rescue of Newcastle Disease virus from Cloned cDNA: Evidence that Cleavability of the Fusion Protein is a Major Determinant for Virulence", J. Virol. vol. 73, pp. 5001-5009 (1999).

Baron, et al., "Rescue of Rinderpest Virus from Cloned cDNA", J. Virol, vol. 71, pp. 1265-1271 (1997).

Ghattas, et al., "The Encephalomyocarditis Virus Internal Ribosome Entry Site Allows Efficient Coexpression of Two Genes from a Recombinant Provirus in Cultured Cells and in Embryos", Mol. and Cell Biology, vol. 11, pp. 5848-5859 (1991).

Elroy-Stein, et al., "Cytoplasmic expression system based on constitutive synthesis of bacteriophage T7 RNA polymerase in mammalian cells", Proc. Natl Acad. Sci, vol. 87, pp. 6743-6747 (1990).

Yum et al., "Functional cDNA Clones of the Human Respiratory Syncytial (RS) Virus N, P, and L Proteins Support Replicatoin of RS Virus Genomic RNA Analogs and Define Minimal trans-Acting Requirements for RNA Replication", J. Virol. vol. 69, pp. 2412-2419 (1995).

Hoffman, et al., "An Infectious Clone of Human Parainfluenza Virus Type 3", J. Virol, vol. 71, pp. 4272-4277 (1997).

Caignard, Grégory, et al., "Measles Virus V Protein Blocks Jak1-Mediated Phsphorylation of STAT1 To Escape IFN-$\alpha/\beta$ Signaling," Virology, vol. 368, 2007, pp. 351-362.

Combredet, Chantal, et al., "A Molecularly Cloned Schwarz Strain of Measles Virus Vaccine Induces Strong Immune Responses in Macaques and Transgenic Mice," Journal of Virology, vol. 77, No. 21, 2003, pp. 11546-11554.

Devaux, Patricia, et al., "Tyrosine 110 in the Measles Virus Phosphoprotein is Required to Block STAT1 Phosphorylation," Virology, 2006, pp. 1-12.

Fields, Bernard N., ed. et al., "Paramyxoviridae: The Viruses and Their Replication," Virology, third edition, 1996, pp. 1197 and 1294.

Ohno, Shinji, et al., "Dissection of Measles Virus V Protein in Relation to its Ability to Block Alpha/Beta Interferon Signal Transduction," Journal of General Virology, vol. 85, 2004, pp. 2991-2999.
Reyes del Valle, Jorge, et al., "A Vectored Measles Virus Induces Hepatitis B Surface Antigen Antibodies While Protecting Macaques Against Measles Virus Challenge," Journal of Virology, vol. 81, No. 19, 2007, pp. 10597-10605.

* cited by examiner

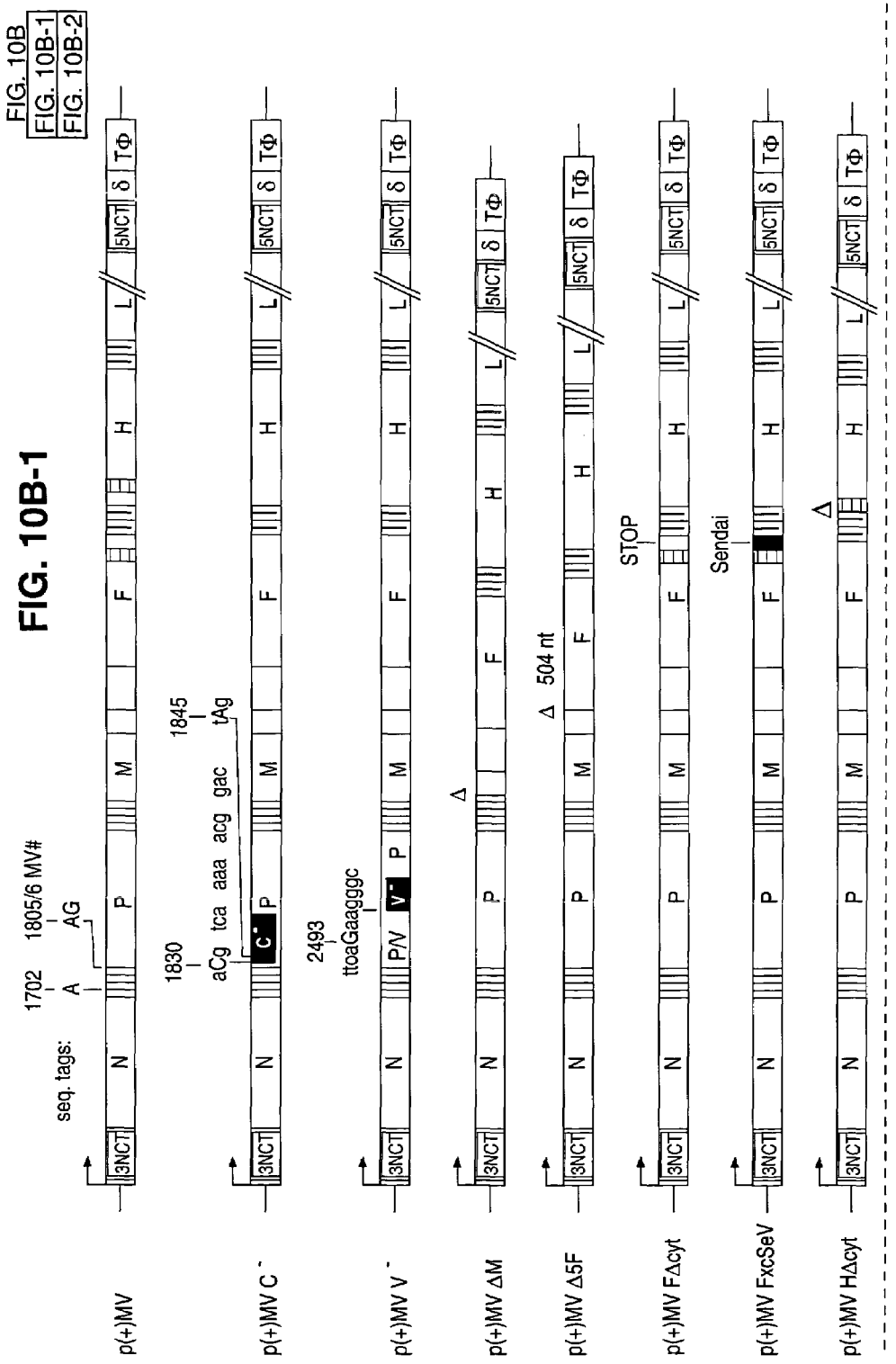

HOST CELLS COMPRISING CDNA CORRESPONDING TO THE ANTIGENOME OF NONSEGMENTED NEGATIVE STRAND RNA VIRUSES, FURTHER ENCODING ANTIGENICALLY ACTIVE PROTEINS

BACKGROUND OF THE INVENTION

Technical Field

The present invention relates, in general, to a methodology for the generation of nonsegmented negative-strand RNA viruses (Pringle, 1991) from cloned deoxyribonucleic acid (cDNA). Such rescued viruses are suitable for use as vaccines, or alternatively, as vectors in somatic gene therapy applications. The invention also relates to cDNA molecules suitable as tools in this methodology and to helper cell lines allowing the direct rescue of such viruses. Measles virus (MV) is used as a model for other representatives of the Mononegavirales, in particular the family Paramyxoviridae.

The invention provides the technology for construction of recombinant vaccine strains, in particular MV vaccine strains containing coding regions for the expression of epitopes or entire protein from other viruses, bacteria, or parasites. It also demonstrates that chimeric MV strains containing heterologous envelope proteins can be constructed suitable for targeting cells not containing an MV receptor. Thus, in principle, plasmids based on the genome of MV, packaged in envelopes containing proteins for targeting special cell types can be constructed, encoding gene products either lacking in genetically defective individuals or toxic for targeted malignant cells.

By straightforward replacement of the MV-specific helper cell lines described in this invention by cell lines expressing the cognate proteins encoded by other representatives of the Mononegavirales to be rescued, any other member of this viral order replicating in vertebrate cells can be used for the purpose of live vaccines or of vectors for gene therapy instead of MV.

BACKGROUND INFORMATION

Measles Virus

MV is a member of the family Paramyxoviridae. Its genetic information is encoded on a single RNA strand of negative polarity, comprising 15894 nucleotides. The genome is sequentially transcribed from the 3' terminus to yield, in addition to a leader RNA, 6 major capped and polyadenylated messenger ribonucleic acid (RNA) species, each of which encodes one major protein. The genome map is shown in FIG. 1, indicating the genes specifying as the principal products N (nucleocapsid protein)-, P (phosphoprotein), M (matrix protein), F (fusion protein), H (hemagglutinin) and L (large protein=polymerase). Several additional RNA and protein species, in part mentioned in the Table of FIG. 1 complicate this simple picture, but they are not relevant here.

MV is a major cause of acute febrile illness in infants and young children. According to estimates of the World Health Organisation (WHO), one million young children die every year from measles. This high toll arises primarily in developing countries, but in recent years also industrialised countries such as the USA have been affected again by measles epidemics, primarily due to incomplete adherence to immunisation programs (Clements and Cutts, 1995). At present, several live attenuated MV vaccine strains are in use (including the Schwarz, Moraten and Edmonston-Zagreb strains), almost all derived from the original Edmonston strain (Enders and Peebles, 1954) by multiple passage in non human cells (Enders, 1962). For a recent discussion of MV vaccinology including future trends see Norrby (1995). Measles vaccine is usually administered at 15 months of age or, in developing countries, already at 6 months, and has proved to be highly effective, usually providing life-long immunity against MV reinfection eliciting morbidity. To date, the genetic alterations responsible for attenuation of these vaccine strains remain unknown. The proven safety of measles vaccine, combined with its high and long-lasting efficiency, predestines it as an ideal plasmid for the expression of heterologous genes. Such a vaccine may prove as efficient in eliciting long-lasting immune protection against other pathogenic agents as against the vector virus itself. Another possible candidate as vaccination vector is Mumps virus, a distant relative of MV, which is also highly efficaceous and safe as attenuated live vaccine.

Rescue of RNA Virus from Cloned DNA

The study of the replication cycle of a number of RNA viruses has been greatly facilitated by the availability of DNA clones from which infectious virus can be rescued, thus allowing the application of reverse genetics. Initially, the bacteriophage Qβ (Taniguchi et al., 1978) and polio virus (Racaniello and Baltimore, 1981), and subsequently Sindbis virus (Rice et al., 1987) were expressed from cloned cDNA. To date, a large variety of positive-strand RNA viruses, primarily infecting vertebrates and plants, can be rescued from cloned DNA (for a recent review see Boyer and Haenni, 1994). In addition, proviral DNA of retroviruses is infectious. However, attempts to obtain infectious virus from cDNA clones of negative-strand RNA viruses have met with great difficulties. This is due to two properties of these viruses: (i) neither genomic nor antigenomic RNAs are infectious, because they do not serve as mRNAs; and (ii) both transcription and replication require ribonucleocapsids, i.e., rod-like nucleoprotein complexes (RNPs), containing the genomic RNA and several proteins with structural and/or enzymatic function.

Rescue from cloned DNA has been achieved several years ago in the case of influenza virus, a negative-strand RNA virus containing eight genome segments. Their RNPs which are small in size and loosely structured as revealed by the susceptibility of their RNA component to RNase, can be assembled in vitro from RNA and the required viral proteins, N and the polymerase components. Initially, an artificial RNA has been used carrying as a reporter the chloramphenicol acetyltransferase (CAT) coding sequence embedded in the noncoding terminal segments of an influenza virus genome subunit (Luytjes et al., 1989). Later, single authentic or altered genome subunit RNAs transcribed in vitro from cloned DNA were used (Enami and Palese, 1991). The assembled RNPs replicated and transcribed upon transfection into influenza-infected cells, as monitored by CAT production and by rescue of a reasserted influenza virus, respectively. Purification of virus containing the introduced subunit from the vast excess of non-reassorted virus in some cases can be accomplished by selection, for example, using a specific neutralising antibody directed against the protein encoded by the cognate subunit of the helper virus.

In contrast, for the viruses with a nonsegmented negative-strand RNA genome, grouped together in the order Mononegavirales (Pringle, 1991) the much more tightly structured and longer RNPs, containing in addition to the N protein the assembly and polymerase cofactor phosphoprotein (P) and the viral RNA polymerase (large protein, L) have been refractory to functional reassociation in vitro. Therefore, many laboratories approached the rescue of representatives of the Mononegavirales starting out with subgenomic RNAs containing only essential sections of the viral genomes, using viruses to provide the helper proteins required to intracellularly encapsidate and replicate these mini-replicons. First, naturally arising subgenomic RNAs, competing with the viral replication and thus known as defective interfering particle (DI) RNAs (Re, 1991) were used, being substituted later by artificial DI RNAs containing reporter genes, transcribed from appropriately constructed plasmids. These mini-replicons, first devised by the group of M. Krystal (Park et al., 1991) according to the replicon used for the initial influenza rescue model (Luytjes et al., 1989), carry a CAT coding sequence inserted into viral noncoding terminal regions of Sendai virus (SeV) and have been used successfully also for respiratory syncytial virus (Collins et al., 1993; Collins et al., 1991), human parainfluenza virus 3 (Dimock and Collins, 1993), rabies virus (RV) (Conzelmann and Schnell, 1994) and MV (Sidhu et al., 1995).

In all these systems, the essential helper proteins were provided either by the homologous viruses or by the vaccinia vector vTF7-3 encoding phage T7 RNA polymerase (Fuerst et al., 1986) to drive T7-specific transcription of transfected plasmids encoding the required proteins N, P and L as pioneered by Pattnaik et al., (1990). These investigations using mini-replicons have allowed important insights into the noncoding regulatory regions of the corresponding viral genomes and antigenomes (for a recent discussion see Wertz et al., 1994). Adopting the same experimental set up, the rescue of VSV, as RV a member of the Rhabdoviridae, has now also been reported (Lawson et al., 1995).

An important drawback of that method (as well as the method reported for the rescue of negative-strand RNA viruses with a segmented genome) is the involvement of a helper virus which has to be separated from the rescued virus and which can interfere with the replication of the virus to be rescued. For RV and VSV, both belonging to the rigidly structured Rhabdoviridae and replicating to high titers, this is not an important problem. However, in case of loosely structured, polymorphic virions typical for the members of the family Paramyxoviridae and in case of viruses yielding only relatively low titers, the presence of a helper virus would render the recovery of rescued viruses difficult and may well preclude their rescue altogether.

Accordingly, the technical problem underlying the present invention was to provide genetic material useful for the generation of non-segmented negative-strand RNA viruses, preferably of the family Paramyxoviridae and most preferably of measles virus and a system for the recovery of such viruses with reasonable efficiency. The solution to said technical problem is provided by the embodiments characterised in the claims.

Thus the present invention relates to a cDNA molecule for the production of negative-strand RNA virus comprising (a) the entire (+)-strand sequence of a non-segmented negative-strand RNA virus of the family Paramyxoviridae from which anti-genomic RNA transcripts bearing the authentic 3'-termini can be transcribed; operatively linked to (b) an expression control sequence.

Accordingly, the present invention relates to a cDNA molecule for the production of any negative-strand RNA virus of the family Paramyxoviridae. Preferably said antigenomic RNA transcripts also bear the authentic 5'-termini.

As has been further found in accordance with the present invention, effective production of measles virus which is a negative-strand RNA virus of the family Paramyxoviridae, is only obtained if the replicons specified by said cDNA molecule consist of an integral multiple of six nucleotides. This phenomenon will also be referred to as the "rule of six" throughout this application. The cDNA molecules of the present invention can conveniently be used for the rescue of negative strand RNA viruses of the family Paramyxoviridae.

In a preferred embodiment of the present invention, in said cDNA molecule, the expression control sequence (b) is an RNA polymerase promoter.

The present invention further relates to a plasmid containing the cDNA molecule of the invention. The plasmid of the present invention is capable of propagation and preferably also expressing the cDNA molecule of the invention as an antigenomic RNA.

In a preferred embodiment, said plasmid contains an expressible DNA fragment which replaces a preferably homologous DNA region of said cDNA molecule, or provides additional genetic information.

As was also found in accordance with the present invention, in the case of MV-based replicons the rule of six must be obeyed, if a foreign—homologous or heterologous—expressible DNA fragment is inserted into the plasmid containing the cDNA of the invention. In other words, any newly created replicon specified by appropriately constructed cDNA molecules will only be capable of yielding reasonable amounts of the desired product, if it obeys the rule of six.

In a most preferred embodiment, said plasmid is characterised in that the expressible DNA fragment is inserted into or adjacent to a region of said cDNA encoding a viral protein, said insertion being effected in a manner maintaining the reading frame to create a fusion protein and permitting the expression of said DNA fragment under the control of the signal sequences of said viral protein. In accordance with the present invention it is anticipated that in various cases appropriate C-terminal extensions of viral proteins will not interfere with their functionality.

In variation to the above described preferred embodiment and also comprised by the present invention, the expressible DNA fragment is expressed in such a manner downstream of a viral protein coding region to avoid formation of a fusion protein, but nevertheless allowing expression of the downstream coding sequence either by a stop/restart mechanism where the last A residue of the upstream termination triplett coincides with that of the start codon of the downstream coding region, or by placing an internal ribosome entry site (IRES) between the two coding regions; see example 12, second paragraph.

In a further most preferred embodiment, said plasmid is characterised in that the expressible DNA fragment is inserted into a non-coding region of said cDNA and flanked by viral signal sequences or heterologous signal sequences controlling the expression of the RNA fragment specified by said DNA fragment; see example 12, first paragraph.

Most preferably, the expressible DNA fragment is placed upstream of the N gene. As has been found in accordance with the present invention, the positioning of said expressible DNA fragment at the 5' end of the MV sequence results in a particularly strong expression thereof; see also Example 14.

Examples of this embodiment, creating additional transcription units, are provided by the plasmids specifying MVs expressing the heterologous CAT reading frame shown in FIG. 10.

A further preferred embodiment of the invention relates to a plasmid comprising a genomic ribozyme sequence immediately adjacent to the 31 terminal nucleotide of said cDNA molecule and optionally downstream of said genomic ribozyme sequence at least one terminator, preferably the T7 terminator.

The inclusion or a ribozyme sequence into the plasmid of the invention leads to the faithful cleavage of the RNA transcript, thus greatly enhancing the yield of transcripts bearing the correct 3' termini which, in the case of MV, must obey the rule of six.

The person skilled in the art is, naturally, capable of devising other means that result in the generation of the authentic 3' termini. Such means include the use or incorporation of restriction sites at the DNA level, or of tripplehelical DNAs.

In a most preferred embodiment of the plasmid of the invention said genomic ribozyme sequence is the hepatitis delta virus genomic ribozyme sequence.

Figure 2:
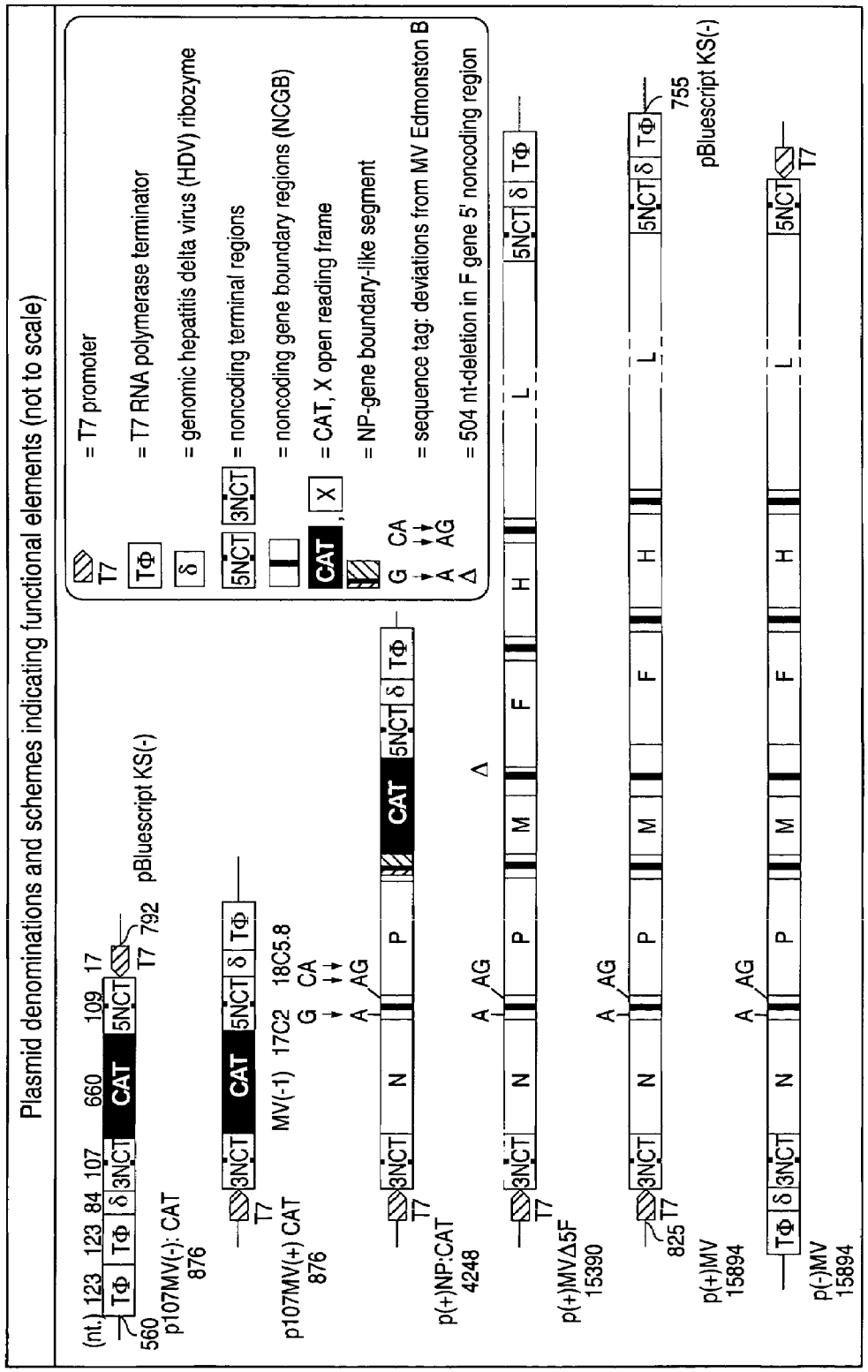

The invention relates in a further preferred embodiment to a plasmid bearing said cDNA which is capable of replicating in a prokaryotic host. A preferred example of such a prokaryotic host is *E. coli*. Illustrations of this preferred example are all cDNA constructs giving rise to modified MVs as shown in FIGS. 2 and 10 demonstrating plasmids replicating to high copy number in *E. coli*.

Additionally, the present invention relates in a preferred embodiment to a plasmid bearing said cDNA(s) which is capable of replicating in a eukaryotic host.

The invention envisages the replication and expression (i.e. transcription, followed by translation of the transcripts formed) of the rescued vector, i.e. the packaged RNA particles (RNPs), in any suitable eukaryotic, preferably vertebrate, host cell. Preferred host cells are those with a high replication and expression capacity. Most preferred are those host cells that allow an easy recovery of rescued viruses for further replication and subsequent formulation in vaccines.

The invention relates in another preferred embodiment to a plasmid wherein said expressible DNA fragment is a DNA fragment being homologous or heterologous with respect to the negative-strand RNA virus and encoding at least one immunogenic epitope.

In a further preferred embodiment of the present invention in said plasmid said expressible DNA fragment encodes at least one immunogenic epitope of at least one pathogen, preferably an envelope protein, at least one gene product lacking in genetically defective individuals or toxic for targeted malignant cells.

This most preferred embodiment of the invention allows for the construction of plasmids as a basis for vaccines that effectively induce an immune response against one or preferably various different pathogens. In the case that the expressible DNA fragment encodes an envelope protein of a different virus than measles virus or of another pathogen, a measles virus based plasmid can be used to target specific cell types usually not recognised by measles virus. Said cell types can then selectively be targeted by rescued viruses specified by the plasmid of the invention and confer to said cell type, for example, a molecule that said cell type is in need of or a toxin, if said cell type is to be eliminated. Naturally, said molecule or toxin is also to be encoded by said-plasmid. The person skilled in the art is capable of devising further applications of this basic principle for which the plasmid of the invention can be used.

Also, said plasmid can encode a product lacking in genetically defective individuals. The rescued virus can then be used for gene therapy of said genetically defective individuals.

Further, malignant cells can be targeted by the rescued virus which is based on the plasmid of the invention and molecules toxic for said malignant cells may be delivered.

In a further most preferred embodiment of the present invention, in said plasmid said expressible DNA fragment is derived from a virus, a bacterium, or a parasite.

A further preferred embodiment of the invention relates to a plasmid wherein said expressible DNA fragment encodes an immunogenic epitope being capable of eliciting a protective immune response.

In a further preferred embodiment, the cDNA molecule or the plasmids according to the invention are based on an RNA virus which is measles virus or mumps virus.

The invention relates further to a prokaryotic or eukaryotic host cell transformed with a plasmid according to the invention. Preferred host cells have been discussed above.

Additionally, the invention relates to a helper cell capable of expressing an RNA replicon from a cDNA molecule of the invention, said cDNA molecule being comprised in the plasmid of the invention or a plasmid comprising a cDNA molecule for the production of negative-strand RNA virus of a family of the order Mononegavirales which is not a member of the family of the Paramyxoviridae, said cDNA molecule comprising the entire (+)-strand sequence, operatively linked to an expression control sequence, and optionally an expressible DNA fragment which replaces a preferably homologous DNA region of said cDNA molecule or provides additional genetic information, said expressible DNA fragment encoding preferably at least one immunogenic epitope of at least one pathogen, which most preferably is capable of eliciting a protective immune response, said cell further being capable of expressing proteins necessary for transcription, encapsidation and replication of said RNA.

Apart from the features described above, the cDNA molecule for the production of negative-strand RNA virus of a family of the order Mononegavirales which is not a member of the family of the Paramyxoviridae may also have in certain embodiments the characteristics of the cDNA molecules of the invention that were discussed herein above, optionally in conjunction with the plasmids of the invention.

In view of the problems the prior art was confronted with for rescuing non-segmented negative-strand RNA viruses, in accordance with the present invention paradigmatic cell lines providing as helper functions T7 RNA polymerase and MV N and P protein were developed. Rescue of MVs can be directly monitored after transfection with plasmids specifying antigenomic RNAs and MV L mRNA. In principle, analogous helper cell lines can be generated for any of these viruses; thus this rescue approach is applicable for all Mononegavirales replicating in vertebrate cells.

Thus, in a preferred embodiment of the helper cell according to the invention said proteins necessary for encapsidation, transcription and replication of said RNA are an RNA polymerase, preferably T7 RNA polymerase and optionally T3 RNA polymerase, and N and P protein, preferably of the virus to be rescued. In accordance with the present invention, said proteins are expressed from stably transfected expression plasmids, henceforth defined as genomic expression.

Since the rescue system now developed, in contrast to the one used for rescue of RV (Schnell et al., 1994), VSV (Lawson et al., 1995) and very recently also for SeV (D. Kolakofsky, personal communication), does not rely on any helper virus, there is no need to separate the rescued virus from the vast excess of any helper virus. Elimination of vaccinia virus from rescued virus is accomplished by a simple filtration step in the case of the rigidly structured virions of Rhabdoviridae but would involve more complex purification schemes in case of pleomorphic Paramyxoviridae, particularly those not replicating to high titers such as MV. Furthermore, for viruses impaired in replication and/or budding by the vaccinia virus, rescue using the prior art systems might fail altogether. Another possible drawback of the prior art systems based on the vaccinia helper virus is the high frequency of DNA recombinations occurring in the cytoplasm of vaccinia virus infected cells which might cause recombination of the plasmid bearing the antigenomic sequence with the plasmids encoding N, P and L protein required for the helper function; this may lead to rescue of viruses containing N, P and L sequences derived in part from the helper plasmids rather than from the plasmid bearing the antigenomic sequence. The helper cell system circumvents all of these problems and should in principle be applicable for the rescue of any of the Mononegavirales replicating in vertebrate cells.

It may not be necessary for the rescue of any single representative of Mononegavirales, to establish a helper cell line expressing the cognate N and P protein (in addition to T7 polymerase). Mini-replicon constructs containing the non-coding terminal regions (NCTs) of canine distemper virus (CDV) which is like MV a morbillivirus, differing from MV in 35% of the nucleotides in the NCTs, replicate in the MV-specific helper cells at an efficiency approaching that of the homologous MV mini-replicon. Thus, possibly CDV could be rescued with the 293-3-46 cells, which were developed in accordance with the present invention and more generally, any helper cell line might be able to rescue a number of not too distantly related Mononegavirales. This will probably depend on the compatibility of the proteins elicited by the related viruses, which was shown not to be the case for SeV-specific N and P and PIV3-specific L (Curran and Kolakofsky, 1991).

For the establishment of new helper cell lines for other viruses which are also envisaged by the present invention, the following considerations might be helpful. The constitutive expression of the T7 RNA polymerase and the MV proteins N and P did not impair the long term stability of the 293-3-46 cell line, as mentioned in the examples attached hereto. Thus, inducible expression of these proteins, for example, by the approaches described by the group of Bujard (for a review see Gossen et al., 1993) will probably not be necessary, although it cannot be excluded that the N and P proteins of other viruses are more deleterious for cell growth than those of MV. Titration of the plasmids used for transfection proved essential, showing that a ratio of about 1:1000 of L-encoding and antigenome-producing plasmid, respectively, was optimal, in agreement with the deleterious effect of high VSV L expression for VSV replication noted by Schubert et al. (1985). An alternative mode of transiently supplying L, using a plasmid containing a CMV promoter/enhancer and an intron upstream rather than downstream of the L coding region to permit some export of the long L mRNA from the nucleus, was also successful in rescue, but the efficiency was not better than with the standard method of cytoplasmic T7-dependent L expression and more than a hundred times more L encoding plasmid was optimal for rescue. In view of these experiences, the decision not to include an L encoding plasmid for the generation of helper cells, thus allowing expression of L at adjustable ratios, was probably advantageous. Nevertheless, it should be mentioned that a cell line stably expressing SeV-derived N. P and L which mediates long term replication of natural SeV DIs has been described (Willenbrink and Neubert, 1994). It is important to note that this cell line differs fundamentally from the helper cells defined in the present invention by its lack of T7 polymerase. As a consequence, no rescue of a virus and not even of a minireplicon from cloned DNA is feasible with this cell line.

In a further preferred embodiment of said helper cell said cell is transfected with at least one of said above described plasmids, said plasmids containing variant antigenomic cDNA of a representative of the Mononegavirales, and is additionally stably transfected with a plasmid comprising DNA encoding the cognate viral L protein.

Thus, instead of selecting for a helper cell that also encodes per se the viral polymerase (L protein), said L protein is transfected into said helper cell on a different plasmid, preferably by cotransfection. Further, a skilled person using the teachings of the present invention is able to create a suitable helper cell line expression also L protein, in which case cotransfection is not necessary.

In a most preferred embodiment of said helper cell, the genes encoding said N, P and L proteins are derived from measles or mumps virus.

In a further most preferred embodiment said helper cell is derived from the human embryonic kidney cell line 293 (ATCC CRL 1573). A preferred example of such a cell is clone 293-3-46 described in the examples.

The invention further relates to an infectious negative-strand RNA virus strain belonging to the order Mononegavirales isolated from the helper cell of the invention.

It must be recalled that five years ago, in an erroneous account, MV rescue was reported by our laboratory (Ballart et al., 1990 and EP-A 0 440 219), using the same basic principle. At that time, the experiments were based on microinjection of initiation complexes, consisting of T7 RNA polymerase and plasmids specifying MV genomes or antigenomes, into a particular cell line containing defective but replicating MV genomes. However, the rescue by microinjection experiments, unfortunately carried out by only one collaborator, could not be repeated, and all purportedly rescued viruses did not contain the genetic tag, as summarised in a commentary to these extremely sad and devastating events (Aldhous, 1992). It is now clear that rescue of MV could not be expected with that experimental setup for several reasons, in particular due to additional nucleotides at both ends of the generated RNAs and due to a cloning mistake rendering the RNA incompatible with the rule of six (Calain and Roux, 1993; the present invention).

The rescue efficiency, in comparison to rescue of positive-strand RNA viruses (Perrotta and Been, 1990), is low, since only 1 to 6 out of $10^6$ transfected cells, each exposed on average to about $2.5\times10^5$ molecules of antigenomic and 80 to 800 molecules of L-encoding plasmid, trigger the formation of syncytia. Nevertheless, in comparison with the rescue method described for RV and VSV, where about $2\times10^7$ cells are transfected to obtain one rescue event (Lawson et al., 1995; Schnell et al., 1994), the MV rescue compares well, particularly in view of the fact that the MV genome size is roughly 4.5 kb larger and thus in principle more difficult to rescue. Importantly, the low efficiency should not constitute a difficulty for the rescue of MV variants replicating only to titer levels even orders of magnitude lower than the Edmonston B strains, since the bottle-neck of rescue is constituted most likely by an early event. It is important to note that on cells fixed at various times after transfection, immunofluorescence indicating H or M gene expression was monitored exclusively in syncytia and there was no indication that rescue was confined to single cells.

When rescue is visible directly by syncytia formation, already thousand of progeny MV genomes have arisen; impaired and thus slowly replicating virus variants might not form visible syncytia initially, but should be revealed after splitting of the transfected cell culture or upon seeding onto fresh Vero cells.

The invention further relates to a method for the production of an infectious negative-strand RNA virus belonging to the order Mononegavirales, comprising the steps of (a) transfecting the helper cell of the invention with any one of the plasmids described above and comprising antigenomic DNA from a virus belonging to the order Mononegavirales (first vector) and optionally a plasmid comprising DNA encoding the viral L protein (second vector); and (b) recovering the assembled infectious negative-strand RNA viruses.

Transfection with the second vector is not necessary, if the helper cell genomically expresses the viral L protein.

In a preferred embodiment of the method of the invention, the ratio of the first vector and the second vector is about 1000:1.

In accordance with the present invention it has been shown that the above ratio is optimal for transfection efficiency.

In further preferred embodiments of the method of the invention, said-recovery is either directly effected from the transfected helper cell culture after syncytia formation or, after mixing of detached helper cells with any other cells competent of being infected and replicating the assembled RNA viruses.

The invention relates further to a vaccine comprising the RNA virus according to the invention which optionally is obtainable by the method of the invention described above, optionally in combination with a pharmaceutically acceptable carrier.

The advantages of the vaccine of the present invention will be briefly discussed below.

In the past, a variety of DNA viruses and positive-strand RNA viruses have been used as carriers to direct the expression of heterologous genes or gene segments in host cells, mainly with the aim to elicit immune protection against the pathogen from which the heterologous genetic material was derived. The main advantage of using such live vaccines is their ability to multiply and typically infect a variety of different cell types, generating the antigens of interest intracellularly which can therefore be presented efficiently to the immune system, thus facilitating the induction of both T cell help and cytotoxicity. In contrast, killed vaccines or proteins manufactured by recombinant DNA technology are much less efficient, even by administration in various particulate forms developed recently, which are more efficient than traditionally used adjuvants. In addition, such vaccines typically induce no mucosal immunity, which is very important for protection against pathogens entering by the respiratory or intestinal route. Failure to induce mucosal immunity is also typical for the immunisation approach using injection of naked DNA encoding antigens.

On the other hand, most replicating vaccines constitute a possible threat, even if they are not proliferating, such as avipox vectors in humans (Baxby and Paoletti, 1992). Complex viral vectors (e.g. based on vaccinia virus and related pox viruses, adenoviruses of herpesviruses) and bacterial vectors (e.g. based on derivatives of the agents causing tuberculosis or cholera) inherently elicit many lateral, unnecessary and/or undesired immune responses. In addition, DNA integration in the genome of infected or transfected cells bears at least the potential for malignant transformation. Multiauthored assessments of various types of vaccines have been published recently (Vaccines and public health; Internat. J. of techn. Ass. in Health care 10, 1-196 1994; Science 265, 1371-1451, 1994), from which the particular benefits of small RNA-based live vaccines are evident.

Several engineered positive-strand RNA viruses have been described for potential use as vectors for immunisation purposes; early examples include poliovirus (Burke et al., 1988) and Sindbis virus (Xiong et al., 1989) and among several more recent accounts, involving larger polypeptide fragments expressed from various representatives of the Picornaviridae, just one should be mentioned here (Andino et al., 1994).

However, it must be stressed that the use of RNA viruses as vectors for vaccination purposes crucially depends on the stability of the foreign genetic material during the replication of the virus. This is not a trivial problem, because these viruses rely on a polymerase devoid of proofreading activity. Said problem has advantageously been solved by the present invention: in comparison to vaccine vectors based on positive-strand RNA viruses as mentioned above, the vaccine of the invention as exemplified by MV-based di- or multivalent vaccines show several important advantages which are valid in principle for any other member of the Paramyxoviridae such as mumps virus. First, the size of inserts is not a priori limited by a requirement to fit into an icosahedral protein shell. Second, the tight encapsidation of the genomes of Mononegavirales obviates RNA secondary structure which is very important in case of the positive-strand RNA viruses over the whole genome length to allow proper replication without annealing of the product to the template RNA strand; RNA segments encoding foreign antigens are not evolved to meet such requirements. Third, due to the modular set up of the genome, different insertion sites and expression modes, either as additional transcription units or as elongation of existing transcription units, expressing the inserted downstream reading frames by stop/restart or by an internal ribosome entry site can be envisaged, thus allowing a large range of different expression levels according to the position within the MV transcription gradient. Fourth, due to extremely low recombination frequencies, Mononegavirales can be expected to retain nonessential genetic material much more stably than positive-strand RNA-viruses. Finally, the rule of six, valid for MV as was found in accordance with the present invention and for other Paramyxovirinae (Calain and Roux, 1993), but as judged from cognate mini- and midi-replicons, not for Rhabdoviridae (Conzelmann and Schnell, 1994) or for Pneumovirinae (Collins et al., 1993), should even increase the faithful retention of foreign coding regions inserted in Paramyxovirinae in comparison to other Mononegavirales. Such an additional genetic stability can be anticipated because only one in six adventitiously arising large deletions and no small insertion or deletion of 1 to 5 nucleotides in a region nonessential for viral replication are expected to lead to viable progeny.

Further, knowledge of the nucleotide sequence variants conferring attenuation will allow to change the coding sequences not implicated in attenuating properties according to the evolution of the viruses over the years thus permitting to "update" the vaccines without incurring the danger of losing the quality of attenuation.

The invention additionally relates to the use of the plasmid of the invention in somatic gene therapy.

Since viral envelope proteins can be exchanged among different representatives of Mononegavirales, as shown here by the replacement of the MV envelope proteins with the VSV glycoprotein, it seems feasible to target the replion based on the replication machinery of Mononegavirales to particular cell types; thus, certain applications in somatic gene therapy can be envisaged. Advantages in comparison to existing vectors for gene therapy include their small size, thus limiting antigen reactions to a few proteins, and their complete inability to integrate into DNA and thus to transform cells.

Additionally, the invention relates to the use of the plasmid of the invention for targeting special cell types. An outline of such targeting schemes and applications has been provided above.

The invention relates further to the use of the plasmid of the invention for the functional appraisal of mutations found typically in MV variants responsible for fatal subacute sclerosing panencephalits or for the identification of mutations responsible for attenuation of Paramyxoviridae strains, preferably measles virus strains.

Finally, the invention relates to a diagnostic composition comprising at least one cDNA molecule of the invention and/or at least one plasmid of the invention.

THE FIGURES SHOW

FIG. 1: Genomic map of measles virus

FIG. 2: Plasmid vectors specifying RNAs with correct MV-specific termini. The numbers below the plasmid names indicate the length in nucleotides of the RNAs generated after ribozyme self-cleavage.

Genomic or antigenomic sense of the specified RNAs is indicated by (−) and (+), respectively.

Note that the MV nucleotide sequences present in these plasmids deviate in 30 positions from EMBL accession No K01711, most notably by a deletion of an A residue at pos. 30, compensated by insertion of an A at pos. 3402. For a commented overview of a MV consensus sequence see Radecke and Billeter (1995).

Figure 3:
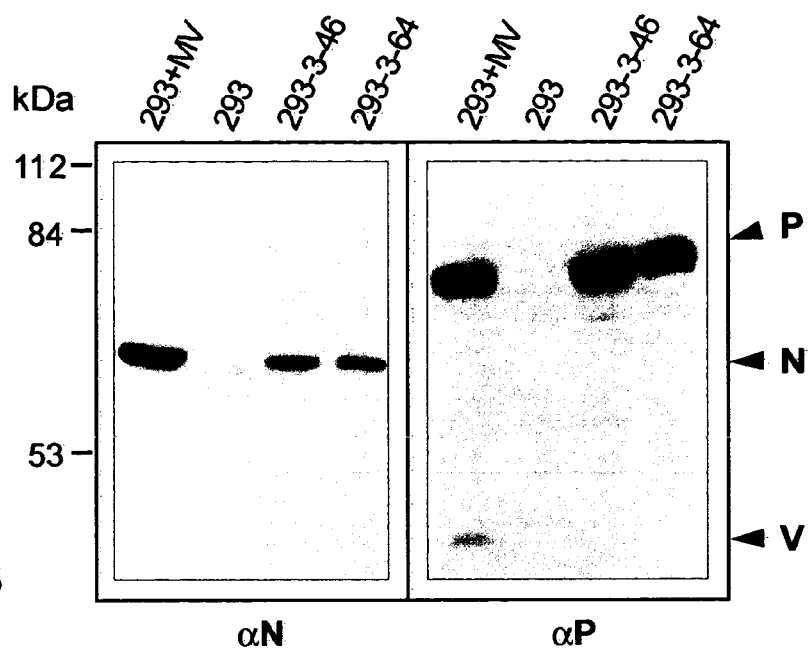

FIG. 3: Western blot showing the expression of MV N and P proteins in MV-infected 293 cells, uninfected 293 cells and in cell line clones 293-3-46 and 293-3-64, respectively. Arrows indicate the position of the structural MV N and P proteins as well as the nonstructural V protein arising from MV P gene transcript editing.

FIG. 4: Overview of experimental components and procedures for rescue A: Mini-replicon rescue, implicating transfection of in vitro transcribed RNA and coinfection with MV, supplying helper proteins N, P and L (and for later stages also M, F and H, as well as nonstructural proteins C and V). B: MV rescue, implicating transfection of plasmid DNAs into helper cells mediating both artificial T7 transcription and N and P functions. For explanation of most symbols see FIG. 2. The L encoding plasmid pEMC-La contains an internal ribosome entry site derived from encephalomyocarditis virus (stippled oval, EMC IRES), fused to the L coding region such that the initiator AUG of EMCV and L coincide; a poly dA tract downstream (about 40 dAs) is indicated as pdA. These two devices ensure transcript stability as well as efficient translation from the transcripts generated in the cytoplasm.

Figure 5:
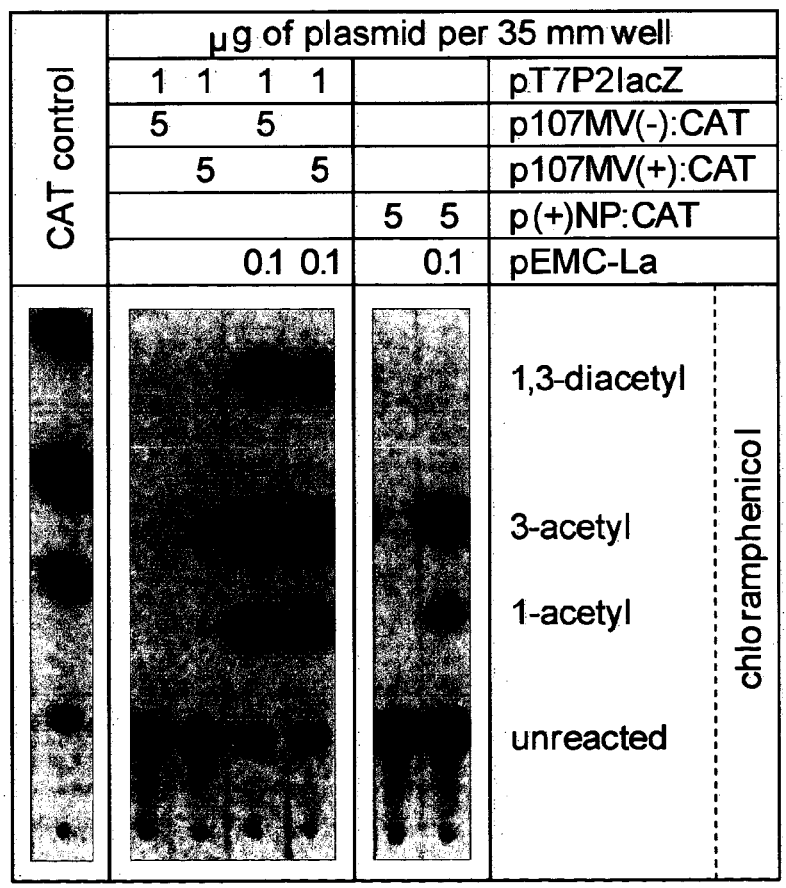

FIG. 5: Assay of CAT activity elicited in 293-3-46 helper cells by transfection of the plasmid constructs p107MV(−):CAT and p107MV(−):CAT, specifying mini-replicons, and construct p(+)NP:CAT, specifying a midi-replicon. The backbone of the plasmid pT7P21acZ is similar as described in Pelletier and Sonenberg (1988). The CAT reading frame of the original plasmid is replaced by the lacZ reading frame.

Figure 6:
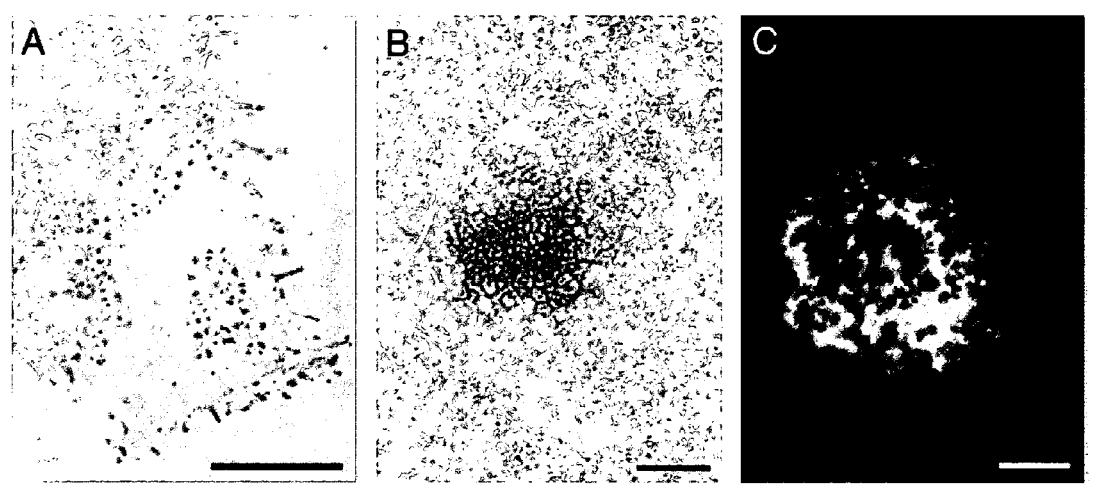

FIG. 6: Visualisation of syncytia formed in 293-3-46 helper cells. A: Rescue experiment, viewed by phase contrast microscopy 4 days after transfection. B, C: Cells grown on glass cover slips, fixed 3 days after transfection and viewed by phase contrast (B) or indirect immunofluorescence microscopy using a monoclonal antibody directed against MV M protein (C). Similar results were obtained with an antibody against H. The bar length represents 100 µm.

Figure 7:
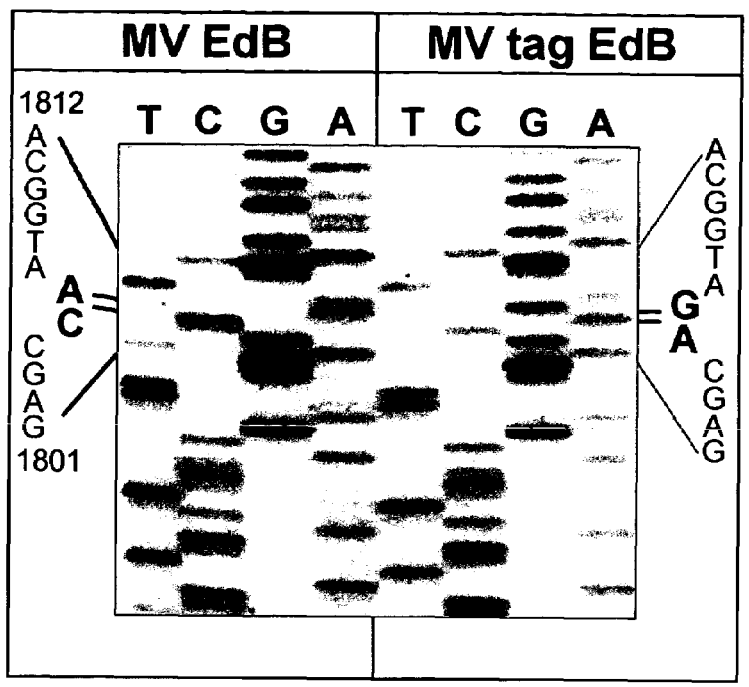

FIG. 7: Sequence determination of plaque-purified viruses, carried out by RT-PCR followed by cycle sequencing as described in the Examples. The left lanes of the relevant area reproduced from a sequencing gel relate to our laboratory Edmonston B strain, the right lanes to the rescued virus. Nucleotide positions indicated correspond to those in the MV consensus sequence as defined in FIG. 2.

Figure 8:
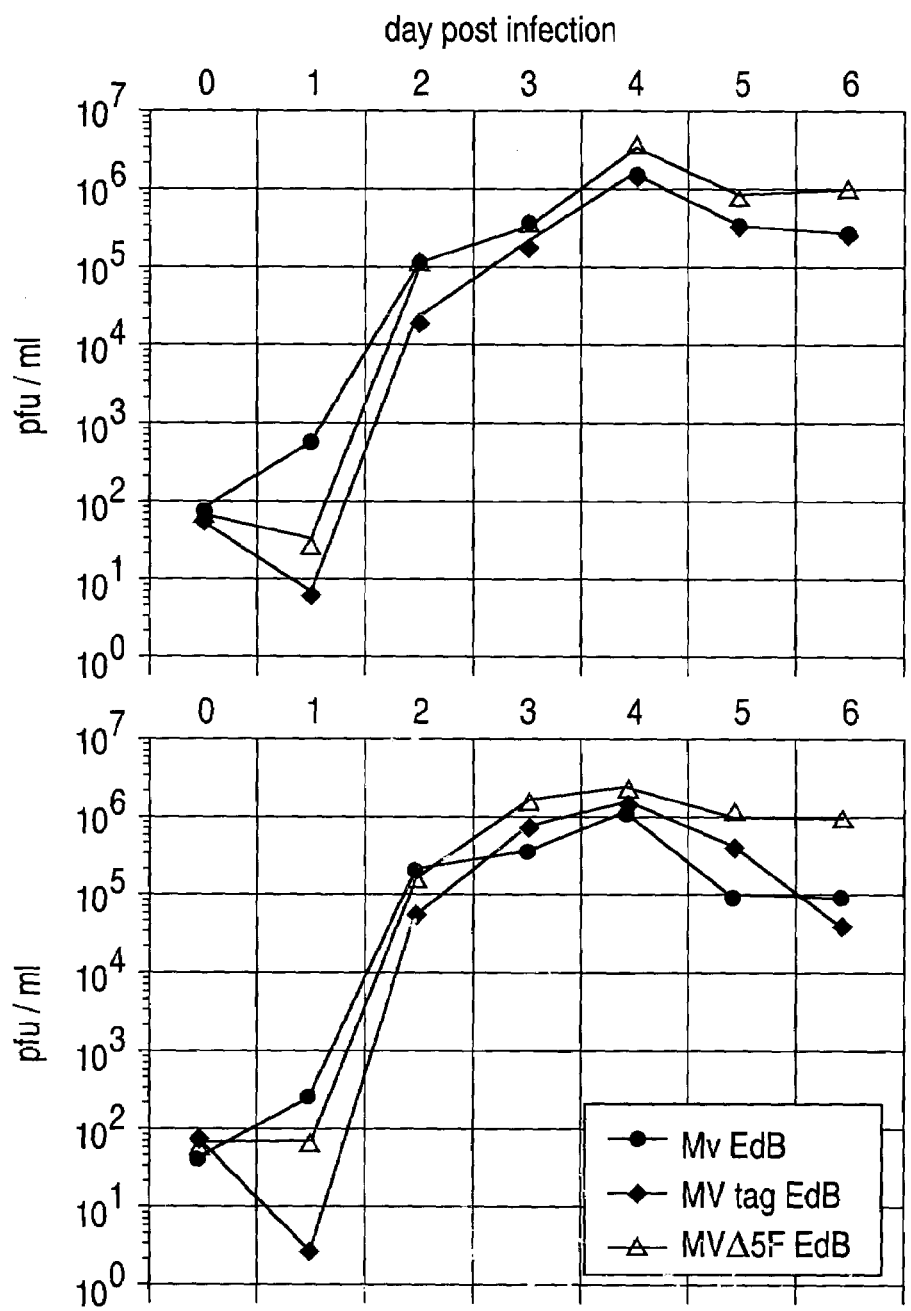

FIG. 8: Replication behaviour of plaque-purified viruses, evaluated by an overlay technique as described in the Examples. The derivatives of rescue experiments, the standard MV tag EdB and the 504 nucleotide deletion mutant MVΔ5F EdB are compared with a clone from our laboratory Edmonston B virus strain. The results of two independent experiments using a representative clone of each virus species are shown.

Figure 9:
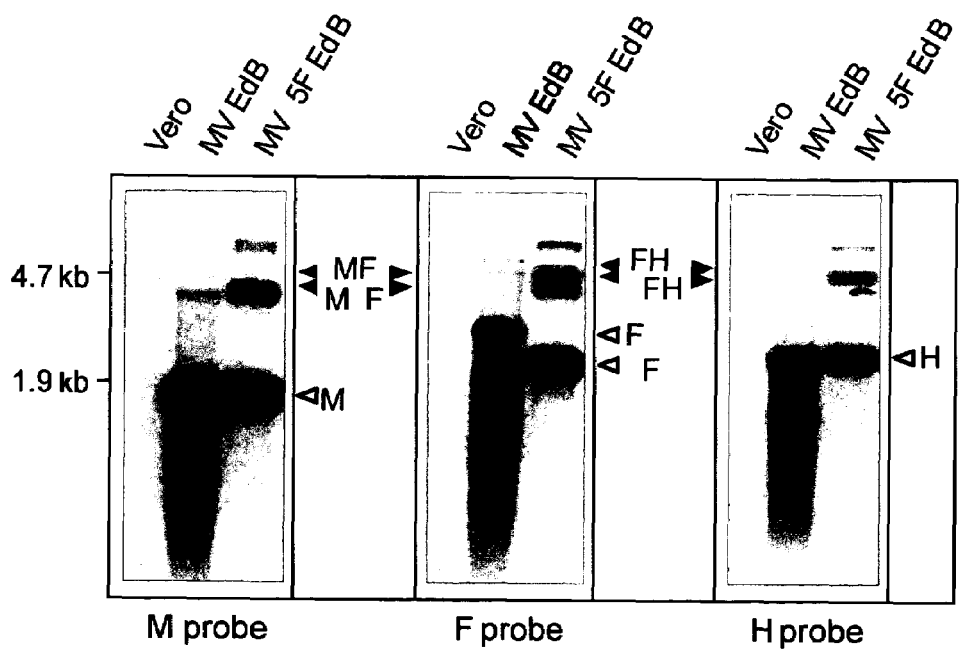

FIG. 9: Northern blots revealing mRNAs of the rescued MV derived from p(+)MV, and the MV deletion mutant derived from p(+)MVΔ5F (FIG. 2). The monocistronic F, M and H mark species (open triangles) and the bicistronic MF and FH mRNAs (black triangles) are revealed by M, F, and H-specific probes. The F-specific mono- and bicistronic RNAs induced by the deletion mutant are clearly smaller than the corresponding RNAs induced by the rescued standard MV (ΔF, 1869 rather than 2372 nt. calculated, without considering poly A tails; MΔF, 3338 rather than 3842 nt., and ΔFH, 3830 rather than 4334 nt.).

Figure 10A:
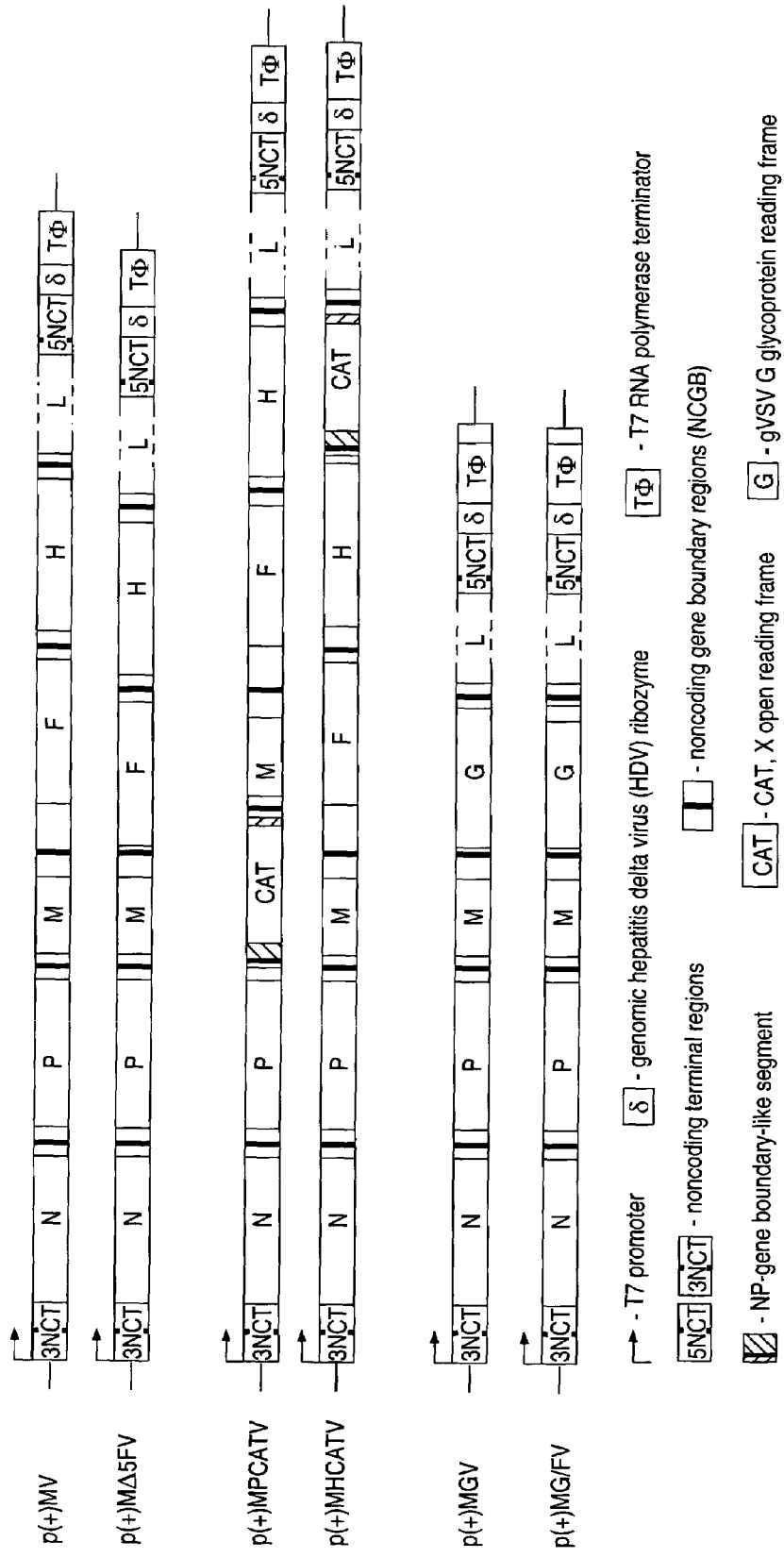

FIG. 10(a) Plasmids for production of standard and deleted MVs and hybrid Kvs containing additional genes or exchanged envelope proteins.

Note that two MV chimeric clones recovered from p(+)MPCATV and from p(+)MHCATV after 10 cycles of infection still expressed CAT activity encoded by the additional transcription unit in every one of the 10 clones taken from the tenth cycle tested.

Figures 2, 10B:
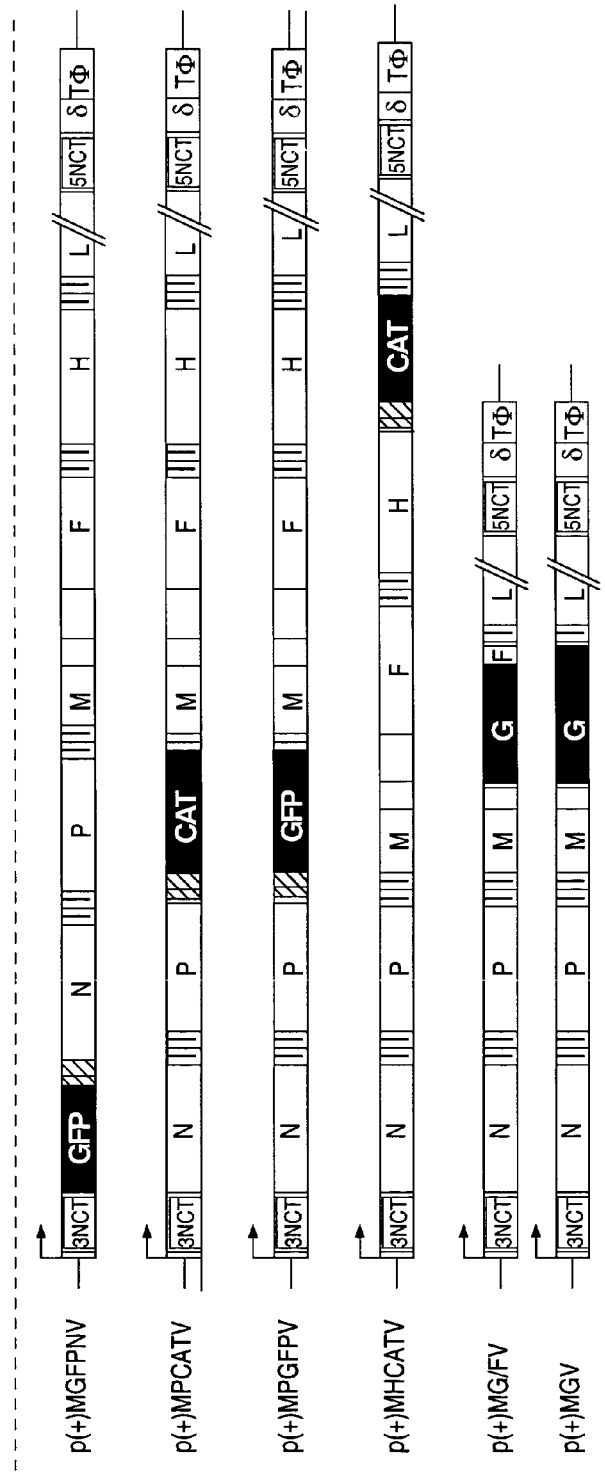

FIG. 10B-1 Plasmids for production of standard and variant Edmonston B measles viruses p(+)MV: The RNA polymerase provides anti-genomic MV RNA with two sequence tags in positions 1702 (A) and 1805 (AG)

(+)MV C⁻: The antigenomic RNA corresponds to that obtainable from p(+)MV with the exception that the C-protein ORF is rendered non-functional by the introduction of two point mutations in positions 1830 (C) and 1845 (A).

p(+)MV V⁻: The antigenomic RNA corresponds to that obtainable from p(+)MV with the exception that the V protein ORF is rendered non-functional by mutating the conserved "editing site".

p(+)MV ΔM: The antigenomic RNA corresponds to that obtainable from p(+)MV with the exception that the complete ORF of the M gene (Δ320 amino acids) with the exception of 15 amino acids has been deleted.

p(+)MV Δ5F: The antigenomic RNA corresponds to that obtainable from p(+)MV with the exception that a deletion of 504 nucleotides (nucleotides 4926-5429 are missing) has been introduced into the F gene.

p(+)MV ΔM: The antigenomic RNA corresponds to that obtainable from p(+)MV with the exception that the sequence encoding the cytoplasmic part of the F protein has been exchanged by a different fragment encoding the cytoplasmic part of the F protein derived from a SSPE case. A premature stop codon results in a deletion mutant having a deletion in the F protein cytoplasmic domain.

p(+)MV Fxc SeV: The antigenomic RNA corresponds to that obtainable from p(+)MV with the exception that the sequence encoding the cytoplasmic domain of the F protein has been replaced by the corresponding sequence from Sendai virus.

p(+)MV HΔcyt: The antigenomic RNA corresponds to that obtainable from p(+)MV with the exception that the sequence encoding the cytoplasmic domain of the H protein has been replaced by a fragment carrying a deletion.

FIG. 10B-2 Plasmids for production of Edmonston B measles virus chimeras and vectors.

p(+) MGFPNV: The antigenomic RNA corresponds to that obtainable from p(+)MV with the exception that an additional cistron has been incorporated upstream of the MV N-ORF that allows MV dependent expression of the reporter gene encoding green flourescent protein; said ORF is inserted into a multiple cloning site.

p(+)MPCATV: The antigenomic RNA corresponds to that obtainable from p(+)MV with the exception that an additional cistron has been incorporated downstream of the P ORF allowing the expression of the CAT gene.

p(+) MPGFPV: The construct corresponds to p(+)MP-CATV with the exception that the CAT coding sequence has been replaced by the GFP coding sequence which is, again, cloned into a multiple cloning site.

p(+)MHCATV: The antigenomic RNA corresponds to that obtainable from p(+)MV with the exception that an additional cistron has been inserted downstream of the H ORF which allows the expression of the CAT gene.

p(+)MG/FV: The antigenomic RNA corresponds to that obtainable from p(+)MV with the exception that the MV F and H genes have been replaced by a gene encoding an VSV G protein, the cytoplasmic part of which has been replaced by the cytoplasmic part of the MV F protein.

p(+)MGV: The antigenomic RNA corresponds to that obtainable from p(+)MV with the exception that the MV F and H genes have been replaced by a gene encoding an VSV G protein.

Figure 11:
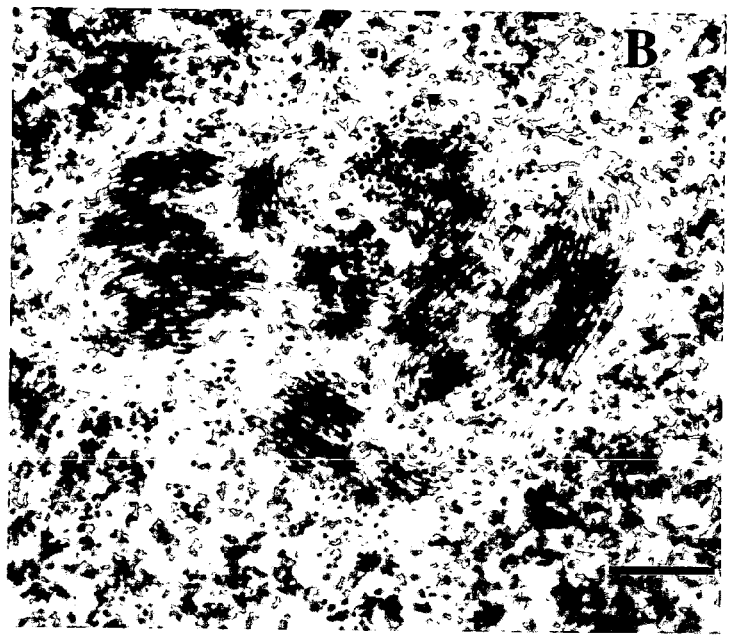

FIG. 11: Electron microscopy of BHK cells infected with replicating agent rescued from p(+)MGV.

Large arrays of RNPs typical for KV-infected cells are visible, showing unimpaired replication capability of the chimeric viral RNA.

Figure 12:

FIG. 12: Electron microscopy of BHK cells infected with replicating agent rescued from p(+)MGV.

Pleomorphic particles resembling MV virions are formed despite the fact that in these infected cell cultures exclusively VSV G protein and no trace of the MV envelope proteins F and H was detectable by Western blotting.

Figure 13:
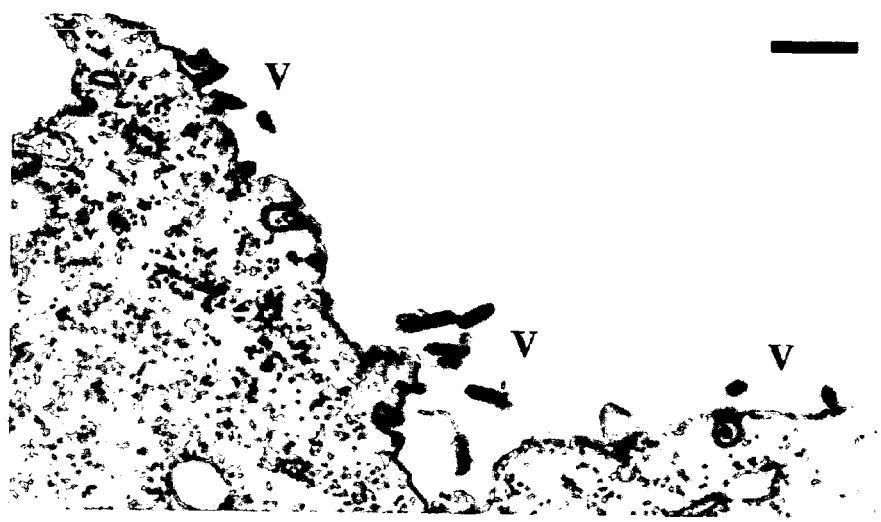

FIG. 13: Electron microscopy of BHK cells infected with VSV: VSV virion particles.

The typical bullet-shaped VSV virions differ completely from the pleomorphic MV-like particles shown in FIG. 12.

The examples illustrate the invention:

EXAMPLE 1

Cells and Viruses

Cells were maintained as monolayers in Dulbecco's modified Eagle's medium (DMEM) supplemented with 5% foetal calf serum (FCS) for Vero cells (African green monkey kidney), with 10% FCS for 293 cells (human embryonic kidney) and with 10% FCS and 1.2 mg/ml G418 for the stably transfected 293 derived cell clones.

To grow MV virus stocks reaching titers of about $10^7$ pfu/ml, recombinant viruses were propagated in Vero cells, and the vaccine strain Edmonston B was grown in Vero or 293 cells. One round plaque-purification was carried out by transferring a syncytium to a 35 mm Vero cell culture which was expanded to a 175 cm$^2$ dish. Virus stocks were made from 175 cm$^2$ cultures when syncytia formation was pronounced. Cells were scraped into 3 ml of OptiMEM I (GIBCO BRL) followed by one round of freezing and thawing. The virus titrations were carried out on 35 mm Vero cell cultures. After 2-3 h of virus adsorption, the inoculum was removed and the cells were overlaid with 2 ml of DMEM containing 5% FCS and 1% SeaPlaque agarose. After 4-5 days, cultures were fixed with 1 ml of 10% TCA for 1 h, then UV-cross linked for 30 min. After removal of the agarose overlay, cell monolayers were stained with crystal violet dissolved in 4% ethanol, and the plaques were counted.

EXAMPLE 2

Generation of Cell Line 293-3-46

Before the transfection, all plasmids were linearized by digestion with SfiI and sterilised by ethanol precipitation. Cells were seeded into one 35 mm well for transfection during 13 h as described below. The transfection mix contained 5 µg of pSC6-N, 4 µg of pSC6-P, and 1 µg of pSC6-T7-NEO. Then, cells were washed once with 2 ml of phosphate buffered saline (PBS; 137 mM NaCl, 2.7 mM KCl, 8 mM Na$_2$HPO$_4$, 1.5 mM KH$_2$PO$_4$), and DMEM containing 10% FCS was added. After 2 days in culture, the cells of the 35 mm well were splitted to two 75 cm$^2$ dishes, and selection under 1.2 mg/ml G418 was started changing the medium every second day. After ~2 weeks, the first clones of a total of ~100 clones were transferred to 5 mm wells. When a clone had expanded to a 21 mm—or 35 mm well, cells were seeded for screening. The expression of the MV N and P proteins was analysed by Western blotting (see also below) using ~⅓ to ⅒ of the total lysate of a confluent 21 mm well. To monitor the functionality of the T7 RNA polymerase, a 35 mm cell culture was transfected with 4 µg of pEMC-Luc (Deng et al., 1991), and the luciferase activity in 1/125 of the cleared total lysate (Promega protocol; harvest 1 day after transfection) was measured in a luminometer. Clones expressing the MV N and P proteins comparable to the same number of 293 cells infected with MV and showing a T7 RNA polymerase activity as high as possible were chosen to test their performance in allowing MV DI RNAs to express CAT. Here, 5 µg of the plasmids p107MV(+):CAT, p107MV(−):CAT, or p(+)NP:CAT with or without 100 ng of pEMC-La were transfected. After 1 day, cells were lysed, and ¼ of the cleared lysates was tested for CAT activity.

EXAMPLE 3

Plasmid Constructions

All cloning procedures were basically as described in Sambrook et al. (1989). PCR amplifications were carried out using the proofreading Pfu DNA polymerase (Stratagene) and primers with a 31 terminal phosphorothioate bond instead of a phosphodiester bond (Skerra, 1992). DNA sequences of the synthetic oligonucleotides are given in lower case for non-MV nucleotides and in upper case for the MV nucleotides; sequences of relevant restriction endonuclease recognition sites are underlined. The construction of the plasmid p107MV(−) :CAT can be found in Sidhu et al., 1995. Plasmid p107MV(+) :CAT is the analogue of the plasmid p107MV(−) :CAT. The additional intercistronic region of p(+)NP:CAT that is similar to the N-P intergenic boundary was constructed by inserting (5'-ctaGCCTACCCTCCAT-CATTGTTATAAAAAACTTAGG CACACAGCCGC-CAGCCCACAACgcgtatcgcgata(+) 1717-1782) and the internally complementary oligonucleotide into the SpeI site of the P gene. The PCR-amplified CAT coding region was inserted as depicted in FIG. 2.

The description of the assembly of the first MV full length DNA, the source of MV nucleotides 2044-14937 in later versions of full length clones such as peuT7MV(−) (see below), is given in Ballart et al., 1990. The main features of the plasmid p(+)MV (FIG. 2) are as follows: The T7 promoter allows the synthesis of the MV antigenomic RNA precisely starting with the first nucleotide. The genomic hepatitis delta virus ribozyme (δ) liberates upon self-cleavage the correct MV 3' terminal nucleotide. Directly downstream of the δ ribozyme, the T7 RNA polymerase terminator Tø stops most of the transcribing polymerases. This ensures that adjacent sequences derived from the vector backbone will not interfere with the cleavage activity. The cloning of p(+)MV started by annealing two internally complementary oligonucleotides #191 (5'-ggggaaccatcgatggataagaatgcggccgcaggtac-3') (SEQ ID NO:2) and #192 (5'-ctgcggccgcattcttatcc atcgatggttccccgc-3') (SEQ ID NO:3) yielding a short polylinker that carries the restriction sites for SacII, ClaI, NotI, and KpnI. This new polylinker replaced the SacII-KpnI fragment in pBloT7 derived from pBluescript KS(+) (Stratagene) containing the T7 promoter fused to a NsiI site (Kaelin, 1989) thus forming the plasmid pBloT7NSCNK. To clone in the 5'-terminal 2041 bp of the MV antigenome (up to the SacII site), a NsiI-digestion was followed by treatment with Klenow polymerase in the presence of all four dNTPs. This created a blunt-end cloning site flush to the nontranscribed part of the T7 promoter sequence. A MV fragment comprising the nucleotides 1-2078 was generated from the 3351 bp PvuI-fragment of peuMV(−) by PCR amplification using prims #182 (5'-ACCAAACAAAGTTGGGTAAGGATAG-3' (SEQ ID NO:4), MV(+) 1-25), and #183 (5'-CAGCGTCGT-CATCGCTCTCTCC-3+(SEQ ID NO:5), MV(−) 2077-2056). Note that the additional A residue at position MV(+) 30 (Sidhu et al., 1995) derived from the MV sequence of peuMV(−) was later deleted by mutational PCR. Upon SacII-treatment, the MV fragment was ligated into the vector to yield pT7MV(+)5'. Next, the 3'-terminus of the antigenome was linked to the sequence of δ followed downstream by Tø. The MV 3'-fragment (nucleotides 14907-15894) was generated from the 14046 bp PvuI-fragment of peuMV(−) by PCR amplification using th primers #186 (5'-GAGAAGCTAGAG-GAATTGGCAGCC-3'(SEQ.ID NO:6); MV(+) 14907-14930) and #187 (5'-ttct gaagactcACCAGACAAAGCTGGG-3'(SEQ. ID NO:7), MV(−) 15894-15879). Another PCR amplification on the plasmid peu3aδTφ with the primers #184 (5'-ataagaat gcggccgcatccggatatagttcctcc-3') (SEQ. ID NO:8) and #FR4 (5'-ttctgaagactcTGGTggccggcatggtcccag-3'(SEQ. ID NO:9), MV(+) 1.5891-15894) yielded the genomic HDV ribozyme linked to the To. Both primers #FR4 and #187 contain close to their 5' ends the recognition sequence for BbsI which creates a sticky end on both fragments comprising the four 3'-terminal MV nucleotides (MV(+) TGGT). After the digestions of the MV 3'-fragment with ClaI and BbsI, of the δ/Tφ-fragment with BbsI and NotI, and of pT7MV(+)5' with ClaI and NotI, a three-way ligation yielded the plasmid pT7MV(+)5'3'δ/Tφ. The final step to generate p(+)MV was to fill in the remaining antigenomic MV nucleotides 2044-14937 by a three-way ligation. The SacII-PacI fragmen: (MV (+) nucleotides 2044-7242) and the PacI-ClaI fragment (MV nucleotides 7243-14937) were released from plasmid peuT7MV(−). These two fragments were ligated into pT7MV (+)5'3'δTφ from which the remaining polylinker (SacII-ClaI) had been removed. The plasmid p(−)MV (FIG. 2) was constructed similarly. The self-cleavage activity of δ was demonstrated by detecting the expected small 3' fragments of in vitro made RNAs on a 5% polyacrylamide/7M urea gel. To generate p (+)MVA5F carrying a 504 nt-deletion (MV(+) 4926-5429) in the 5' noncoding region of the F gene, first a PCR was carried out on plasmid pAeFl (Huber, 1993) using primers #88 (5'-CcGAATCAAGACTCATCCAATGTC-CATCATGG-3' (SEQ. ID NO:10) MV(+) 5430-5461) and #89 (5'-AGAGAGATTGCCCCAATGGATTTGACCG-3' (seq id no:11), mv(−) 5550-5523). The PCR fragment digested with HpaI replaced the NarI-HpaI fragment in pAeF1. The NarI-PacI-fragment of this vector then replaced the corresponding fragment in p(+)MV.

The vector backbone of pEMC-La is based on pTM1 (Moss et al., 1990) in which a NcoI-site overlaps with an ATG trinucleotide. Using this ATG as the start codon, an open reading frame inserted into this NcoI-site is translationally controlled by the encephalomyocarditis (EMC) virus internal ribosome entry site (IRES). The MV L coding sequence linked to an artificial poly(dA)-tract was taken from vector pAeL (Huber, 1993) in two steps: first, a 405 bp fragment containing the MV nucleotides 9234-9630 was generated by PCR using primers #194 (5'-gtggat ccATGGACTCGCTATCTGTCAACC-3'(SEQ ID NO:12), MV(+) 9234-9255) and #195 (5'-AGTTAGTGTCC CTTAAGCATTGGAAAACC-3'(SEQ ID NO:13), MV(−) 9630-9602); second, a 6265 bp fragment comtprising nucleotides 9572-15835 of the MV L gene sequence joined to the poly(dA)-tract was excised with EcoRI. After removing the NcoI-EcoRI part of the polylinker in pTM1 and digesting the PCR fragment also with NcoI and EcoRI, a three-way ligation including the 6265 bp EcoRI-fragment yielded pEMC-La.

To eliminate the T7 promoter located 5' of the CMV promoter/enhancer in the vectors pSC-N and pSC-P (Huber et al., 1991), pSC6-N and pSC6-P were constructed by replacing a PvuI-EcoRI fragment with the corresponding fragment of pSP65 (Promega). pSC6-T7 was generated by exchanging the N gene insert of pSC6-N by the fragment carrying the T7 RNA polymerase gene of pAR 1173 (Davanloo et al., 1984). pSC6-T7-NEO was constructed by ligation of the phosphoglycerol kinase promoter-neomycin-resistance cassette (Soriano et al., 1991) into the unique AvrII site of pSC6-T7 using appropriate linker oligodeoxyribonucleotides. All cloning sites were verified by sequencing.

EXAMPLE 4

Transfectiono f Plasmids and Harvest of Reporter Gene Products

Cells were seeded into a 35 mm well to reach ⁻50-70% confluence when being transfected. 3-8 h before transfection, the medium was replaced with 3 ml of DMEM containing 10% FCS. G418 was omitted henceforth because of its toxic effect during transfection. All plasmids were prepared according to the QIAGEN plasmid preparation kit. The protocol for the $Ca^{2+}$ phosphate coprecipitation of the DNA was adapted from Rozenblatt et al. (1979). The plasmids (2-10 μg per 35 mm well) were diluted with 300 μl of 1× transfection buffer (137 mM NaCl, 4.96 mM KCl, 0.7 mM $Na_2HPO_4$, 5.5 mM dextrose, 21 mM HEPES pH 7.03). 1 M $CaCl_2$ solution was added to a final $Ca^{2+}$-concentration of 125 mM, and the mix was incubated at 20° C. for 30-120 min. The coprecipitates were added dropwise to the culture and the transfection was carried out at 37° C. and 5% $CO_2$ for ⁻15 h. Then, the transfection medium was replaced with 3 ml of DMEM containing 10% FCS. The products of the reporter genes were harvested 24-37 h after transfection. Cells were washed and lysed with Reporter lysis buffer (Promega), and CAT and luciferase assays were done following the supplier's protocol.

EXAMPLE 5

Experimental Set-Up to Rescue MV 293-3-46 cells prepared for transfection as described above were transfected with 5 µg of the plasmid harbouring the MV antigenomic DNA in presence or absence of 1-100 ng of the plasmid specifying the MV L mRNA. First syncytia appeared about 2-3 days after transfection when the cells were still subconfluent. To allow syncytia formation to progress more easily, almost confluent cell monolayers of each 35 mm well were then transferred to a 75 cm² dish. When these cultures reached confluence, cells were scraped into the medium and subjected once to freezing and thawing. Cleared supernatants were used to infect monolayers of Vero cells either to grow virus stocks or to harvest total RNA for analysis.

EXAMPLE 6

RT-PCR, Cycle Sequencing, Northern Blot, Western Blot, Immunofluorescence

For RT-PCR followed by cycle sequencing, Vero cells were infected with cleared virus suspensions either harvested from rescue cultures or from later passages, and total RNA was isolated according to Chomczynski and Sacchi (1987). 2 µg of total RNAs were first hybridised with 10 pmol or 1 nmol of random hexamer primers by heating to 80° C. for 1 min and then quick-cooled on ice. Reverse transcriptions were carried out with 200 U of MMLV-RT (GIBCO BRL) in the presence of 1 mM dNTPs in a buffer containing 20 mM Tris-HCl pH 8.4, 50 mM KCl, 2.5 mM MgCl$_2$, 0.1 mg/ml bovine serum albumin, and 1 U RNAsin (Promega). The mixes were kept at 20° C. for 10 min, incubated at 42° C. for 1 h, and terminated by heating at 95° C. for 10 min. 1/10 of the reaction volumes was used as templates for the PCR amplification with the primers #59 (5'-ACTCGGTATCACTGCCGAGGATG-CAAGGC-3'(SEQ ID NO:14), MV(+) 1256-1284) and #183 (5'-CAGCGTCGTCATCGCTCTCTCC-3'(SEQ ID NO:5), MV(−) 2077-2056). After 40 cycles, the 822 bp fragments were isolated using the QIAquick gel extraction kit (QIAGEN). The sequencing reactions were done according to the linear amplification protocol (Adams and Blakesley, 1991). Primer #76 (5'-ctaGCCTACCCTCCATCATTGT-TATAAAAAACTTAG-3'(SEQ ID NO:15), MV(+) 1717-1749)was used for the tag in the 5' noncoding region of the P gene and primer #6 (5'-ccggTTATAACAATGATGGAGGG-3'(SEQ ID NO:16), MV(−) 1740-1722) for the tag in the 3' noncoding region of the N gene.

Total cellular RNA for Northern blot analysis was isolated from Vero cells using the TRI REAGENT® (Molecular Research Center, Inc.) and poly(A) RNA was purified using oligo(dT)$_{25}$-coated coated super paramagnetic polystyrene beads (Dynal) and a magnetic particle concentrator. The RNA was electrophoresed through a 1% agarose gel in 6% form-aldehyde-containing running buffer and transferred to a Hybond-N$^+$ membrane (Amersham) by capillary elution in 20× SSC. Filters were prehybridised at 42° C. for 4 h. Hybridisation was performed overnight at 42° C. in 50% (v/v) formamide, 1 M NaCl, 10% (w/v) dextran sulfate, 1% SDS, yeast tRNA (0.1 mg/ml) containing 2×10⁶ c.p.m./ml of an [α-³²P] dATP-labeled DNA probe prepared with Prime-It II (Stratagene). The following DNA fragments were used for random priming: the 1.4 kb SalI-BamHI fragment from pSC-M (Huber et al., 1991), the 1.7 kb HpaI-PacI fragment from PCG-F, and the 1.6 kb SmaI-XbaI fragment from pSC-H (Huber et al., 1991). pCG, a eukaryotic expression vector containing a SV40 origin of replication and a CMV promoter/enhancer, was constructed by deletion of the L gene as well as the downstream β-globin splice site of pSC-L (Huber et al., 1991; Severne et al., 1988) and subsequent insertion of the β-globin splice site (from pSG5 Stratagene) upstream of a new polylinker. The pCG-based plasmid pCG-F contains an insert consisting of the entire F gene. Filters were washed in 2× SSC at 20° C. for 10 min and twice in 2× SSC, 1% SDS at 65° C. for 30 min. Bands were visualised by autoradiography.

To analyse the expression of the MV N and P proteins by Western blotting, cells were washed with PBS and cytoplasmic extracts were prepared using 300 µl lysis buffer (50 mM Tris-HCl pH 8, 62.5 mM EDTA, 1% NP-40, 0.4% deoxycholate, 100 µg/ml phenylmethylsulfonyl fluoride, and 1 µg/ml Aprotinin). About 1/60 of the total lysates was run on SDS-8%PAGE and blotted onto Immobilon-P membranes. As first antibodies, either the rabbit polyclonal anti-N antibody #179 (kindly provided by C. Oervell prepared according to standard procedures) in a 6000-fold dilution in TBST (10 mM Tris-HCl pH 7.2-8, 150 mM NaCl, 0.05% Tween 20) or the rabbit polyclonal anti-P antibody #178 (Oervell and Norrby, 1980) in a 3000-fold dilution in TBST was used. The second antibody was a swine anti-rabbit antibody coupled to horseradish peroxidase allowing the visualisation of the bands by the enhanced chemiluminescence kit (ECL™ Amersham Life Science, RPN 2106).

For immunofluorescence microscopy, 293-3-46 cells were seeded for a rescue experiment on 24 mm×24 mm glass cover slips in 35 mm wells, cultured overnight and transfected as described above. 3 days after transfection, cells were permeabilized with acetone:methanol (1:1) and indirect immunofluorescence was performed essentially as described (Hancock et al., 1990; Oervell and Norrby, 1980), except that PBS was supplemented with 1 mM MgCl$_2$ and 0.8 mM CaCl$_2$ and that p-phenylendiamine was omitted from the mountant. Viral M and H proteins were detected using mouse monoclonal anti-M-16BB2 and anti-H-I29 antibodies (Sheshberadaran et al., 1983) and rabbit anti-mouse IgG [F(ab')$_2$] antibodies coupled to rhodamine (Pierce, 31666).

EXAMPLE 7

Genomic and Antigenomic Plasmids Specifying Mini-, Midi-, and Full Length replicons The plasmid constructs used in this study are shown in FIG. 2. p107MV(−):CAT and p107MV(+):CAT specify genome- and antigenome-sense RNAs, respectively, in which all MV coding regions are precisely replaced by the CAT coding region. In MV-infected cells or in helper cells (see below), they give rise to mini-replicons and to capped and polyadenylated CAT mRNA comprising the 5'N and the 3'L noncoding region. p(+)NP:CAT, containing in addition also the MV N and P coding regions in their ordinary MV sequence context, gives rise to midi-replicons. Full length or partially deleted antigenomic or genomic RNAs are specified by p(+)MVA5F, p(+)MV and p(−)MV: For all these plasmids, transcription with T7 RNA polymerase yields RNAs bearing the authentic nucleotides of the viral genomic and antigenomic termini, respectively (Sidhu et al., 1995). Correct initiation was accomplished by direct fusion of the T7 promoter (devoid of its transcribed part) to the genomic and antigenomic sequence. Starting all transcripts with the MV-specific nucleotides ACC rather than the T7-specific GGG reduces the RNA yield by about one order of magnitude, as revealed by in vitro transcription studies using precursor plasmid constructs. To mediate formation of the correct MV 3' termini, the hepatitis delta virus genomic ribozyme sequence (Perrotta and Been, 1990) was cloned immediately adjacent to the MV 3' terminal nucleotides; the introduction of T7 terminators increased the efficiency of self-cleavage.

EXAMPLE 8

Helper Cells Stably Expressing MV N and P Protein as Well as T7 RNA Polymerase The human embryonic kidney cell line 293 was chosen because it is highly permissive for MV. In addition, these cells can be efficiently transfected by the calcium phosphate coprecipitation method; 30 to 60% of the cells stained blue 24 hours after transfection with a plasmid encoding 2-galactosidase. Following cotransfection of 293 cells with pSC6-N, pSC6-P and pSC6-T7-NEO as described in the Examples, about 100 colonies were expanded under neomycin selection. The expression of N and P was screened by Western blotting, and the activity of T7 RNA polymerase was evaluated by transfection with a reporter plasmid containing the firefly luciferase coding region under control of a T7 promoter. Many clones expressed high levels of P, but only few coexpressed N efficiently. FIG. 3 shows N and P expression of two selected cell lines at levels comparable to that of MV-infected 293 cells; T7 RNA polymerase activity detected in clone 293-3-46 was among the highest of all clones whereas it was about 100 times lower in clone 293-3-64 which turned out not to rescue MV. A third cell line, 293-3-43, expressing the three proteins at levels comparable to 293-3-46 was also active in rescue.

The expression of the introduced genes did not reduce the susceptibility for MV infection. The helper cell line 293-3-46 principally used MV rescue, although growing at a rate 2-3 times slower in comparison to the parent 293 line, proved to be very stable and fully functional after more than 80 cell splittings at dilutions 1:4 to 1:8.

EXAMPLE 9

From MV Mini-Replicon Rescue Using Helper MV to MV Rescue Using Helper Cells 293-3-46

The MV rescue system was developed stepwise, permitting to functionally test all components. On one side, MV-dependent rescue of mini- and later successively longer midi-replicons was ascertained by CAT reporter assays. Similarly, on the other side, the functionality of the 293-3-46 cells was compared t the MV-based help described before (Sidhu et al., 1995).

Figures 4A, 4B:
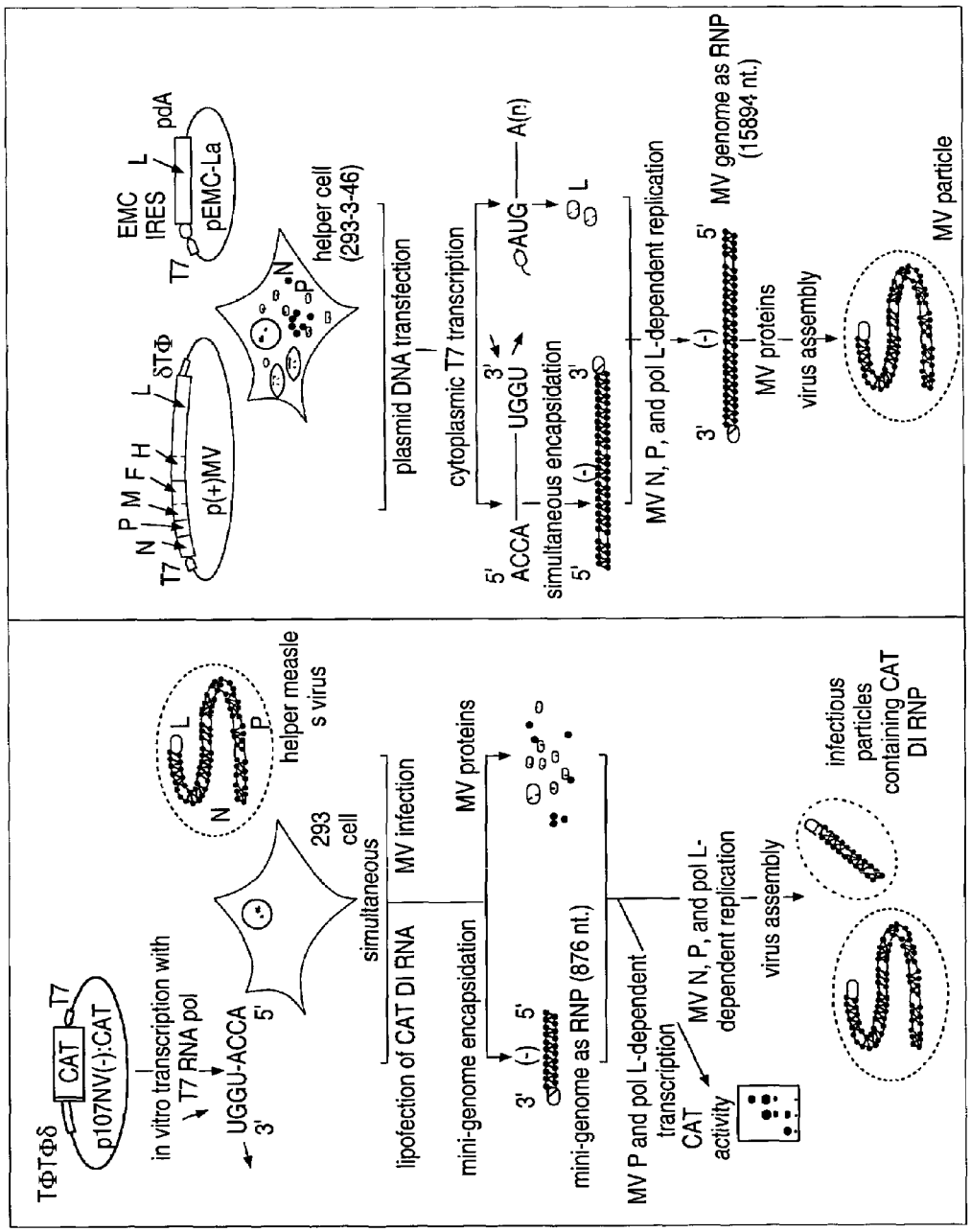

The mini-replicon rescue test is shown schematically in FIG. 4A. Small transcripts from p107MV(−):CAT, p107MV (+):CAT (Sidhu et al., 1995) and later longer transcripts, e.g. generated from p(+)NP:CAT (FIG. 2), behaved like mini- and midi-replicons, respectively. They were encapsidated, transcribed to produce CAT, replicated and packaged into virion particles to infect new cells. During the first 2 to 4 infection cycles, they massively amplified whereas in later cycles replication of both MV and the mini-replicons was curtailed, as observed for naturally occurring DI RNAs (Re, 1991). Analyses of the amplified RNAs showed that the encapsidated replicons and the CAT transcripts contained the respective different MV-specific terminal regions (Sidhu et al., 1995). Most importantly, it turned out that for efficient function, the total number of nucleotides of the replicons had to be a multiple of six, a requirement—termed the rule of six— previously found essential for natural and slightly modified SeV DI RNAs of the copy-back type (Calain and Roux, 1993). Adherence to this rule was crucial for the construction of plasmids specifying a variety of mini- and midi-replicons such as those shown in FIG. 2: This, was also the case for full lengths clones.

The helper function of stably transfected cell clones was tested with the set-up represented in FIG. 4B, using however either plasmid p107MV(−) :CAT, p107MV(+) :CAT or p(+) NP:CAT (FIG. 2) instead of p(+)MV. As shown in FIG. 5, CAT activity arose in the transfected cells, although at levels considerably lower than in 293 cells infected with MV and cotransfected directly with mini- or midi-replicon RNA. The cotransfection of plasmid pEMC-La encoding the MV L protein was an absolute requirement. As expected, low background CAT activity was detected when the plus-sense mini-replicon construct was used. The two constructs containing only the CAT reading frame in the plus- and minus-sense elicited about equal amounts of CAT activity; the midi-replicon construct gave rise to roughly 100 times less CAT activity than the mini-replicon.

The transfection protocol was optimised in terms of maximal achievable CAT activity, using mini- and midi-replicon plasmids. Then, the full length constructs p(+)MV and p(−) MV were tested. About $10^6$ cells contained in each 35 mm well were transfected and we estimate that about one tenth of these actually received full length as well as the L-encoding plasmids. Usually, following cotransfection of p(+)MV and pEMC-La, 1 to 6 syncytia developed after 2 to 3 days in each well. No syncytia were found when the latter was omitted or when the p(−)MV plasmid was used. The rescue experiments were carried out by different experimenters using different DNA preparations. The efficiency was slightly viable, but at least 30% of the transfected wells revealed rescue. FIG. 6 shows typical syncytia formed in these experiments, viewed either directly (phase contrast, 6A) or after fixation of cells grown on cover slips (phase contrast, 6B, or immunofluorescence of the same area, 6C).

EXAMPLE 10

Characterisation of Rescued MV

First, it had to be ascertained that the rescued MVs contained the genetic tag which had been introduced into the MV full length plasmid clones. The 3 nt tag indicated in FIG. 2 originated from a variant 176 nt N/P noncoding gene boundary region (NCGB) recovered from the SSPE-derived MV replicating in IP-3-Ca cells (Ballart et al., 1990). Rescued viruses were amplified in Vero cells, either directly from the transfected cells or after plaque purification; the products recovered by reverse transcription followed by polymerase chain reaction (RT-PCR) were analysed by cycle sequencing. FIG. 7 shows an example of these analyses, revealing the AG tag instead of CA in the Edmonston B strain passaged in our laboratory.

We did not analyse the entire sequence of rescued MVs to exclude any error introduced either during the assembly of the antigenomic plasmid clones or during T7 RNA polymerase transcription in the rescue step. However, major deleterious changes could be ruled out by analysing the replication behaviour of the rescued virus in comparison to that of the Edmonston B strain. FIG. 8 shows that both the speed of replication as well as the final titers reached in repeated experiments were indistinguishable between single plaque-purified normal (MV EdB) and rescued (MV tag EdB) viruses. The apparent different at day 1 after infection was not a consistent observation. Non-plaque-purified virus stocks gave similar results.

EXAMPLE 11

MV Missing 504 Nucleotides int he F Gene 5' NonCoding Region

As a first application of the reverse genetics system, we deleted 504 nucleotides, thus generating a shortened genome compatible with the rule of six mentioned above. This eliminated almost the entire F gene segment of the long enigmatic noncoding M/F NCGB which is typical for MV and the other morbilliviruses, whereas the representatives of the other two genera of the subfamily Paramyxovirinae, paramyxovirus and rubulavirus, contain only a short NCGB. Remarkably, it was viable and moreover it replicated in cell culture at a rate indistinguishable from that of the Edmonston B and the rescued nondeleted MV strain (FIG. 8, MVA5F EdB). To determine the size of the F gene derived RNAs, the MV-specific mRNA induced by these plaque purified viruses was analysed, using probes specific for the F and for the M and H genes situated up- and downstream of F, respectively. Indeed, as shown in FIG. 9, the F MRNA as well as the MF and FH bicistronic RNAs are consistently shorter in cells infected with the MVA5F EdB variant.

EXAMPLE 12

MVs Expressing CAT Activity

To explore the feasibility to express foreign proteins from engineered MV we inserted a CAT reading frame flanked by intercistronic regions into the MV antigenomic cDNA sequence; two positions were tested, on one hand between the N and the P and on the other hand between the H and the L gene (FIG. 10, p(+)MPCATV and p(+)MHCATV, respectively). The intercistronic region flanking the CAT reading frame was deviced according to the intercistronic N/P gene boundary region, but contains additional restriction sites unique in the entire plasmid, suitable for further manipulations. From these constructs, recombinant MVs expressing CAT activity were rescued with about the same efficiency as from the standard and the deleted constructs p(+)MV and p(+)MAA5FV respectively. As expected from the natural transcription gradient typical for all Mononegavirales, p(+) MHCATV expressed somewhat less CAT activity than p(+) MPCATV. Most importantly, the CAT expression of the recombinant viruses seems to be remarkably stable as revealed from the experiment mentioned in the legend to FIG. 12 in which an overall amplification of the recombinant viruses of at least $10^{30}$ was achieved. We actually had expected that viruses rescued from p(+)MPCATV would be less stable than those from p(+)MHCATV, because in the former the transcription of all genes following the inserted CAT are expected to be lower than normal whereas in the latter only the L gene transcription should be lower. Apparently, the position of the insert does not greatly affect the viability of the rescued viruses. However, no competition experiments with standard MV have been carried out so far. Furthermore, it has to be expected that recombinant viruses expressing proteins which actively interfere with MV replication will turn out to maintain the inserted gene less faithfully.

It should be mentioned here that insertion of a foreign coding sequence within existing MV genes should be even less harmful for the viral replication than by creating new transcription units as in the constructs discussed above. The general inability of the eukaryotic translation machinery to express more than one reading frame from a mRNA can in principle be overcome by (at least) two devices: the stop/restart mechanism and internal ribosome entry sites (IRES). Both mechanisms are actually used in special cases for natural protein expression. An example of the first is represented by the translation of the M2 polypeptide in Influenza B virus (Horvath, C. M., Williams, M. A., and Lamb, R. A. (1990) Eukaryotic coupled translation of tandem cistrons; identification of the influenza B virus BM2 polypeptide. EMBO J. 9, 2639-2947). For the second mechanism, many recognized natural precedents exist, most notably the IRES of Picornaviridae (Sonenberg, N. (1990) Poliovirus translation. Curr. Top. Microbiol. Immunol. 161, 23-47), but also IRES in cellular mRNAs such as that specifying BiP (Sarnow, P. (1990) Translation of glucose-regulated protein 78/immunoglobulin heavy-chain binding protein mRNA is increased in poliovirus-infected cells at a time when cap-dependent translation of cellular RNA is inhibited). All of these cited types of device have been explored in the context of the MV N and H genes, using as coding regions downstream of the MV N and H reading frames those yielding CAT and firefly luciferase, respectively, as reporters. The whole bicistronic constructs were expressed from conventional expression plasmids in primate cells and yields of reporter proteins ranging between 10 and 100% in comparison to the proteins encoded by the upstream reading frames were obtained (Diploma theses, University of Zürich, composed by A. Cathomen (1991) and O. Peter (1992)).

EXAMPLE 13

MV Chimera Bearing the VSV Envelope Protein

To explore the feasibility to rescue genetically stable chimeric Mononegavirales in which the envelope proteins of one virus are replaced by the those of another virus p(+)MGV and pMG/FV (FIG. 10) were constructed. In the former construct the entire MV F and H coding regions were replaced by that encoding the VSV G protein which fulfills a receptor binding and a fusion function analogous to those of the MV H and F proteins, respectively. The latter construct was deviced such that a fusion protein is created containing the large exterior part and the transmembrane regions from the VSV G protein fused to the cytoplasmic tail of the MV F protein which is thought to interact specifically with the MV M protein. Indeed, chimeric viruses could be recovered from both constructs which could be distinguished from each other only by slightly different cytopathic effects (which are both drastically different from those elicited by MV) and by the fact that in cells infected by the virus rescued from the latter construct the fusion protein could be revealed by Western blotting not only by antibodies directed to the VSV G exodomain by also to antibodies directed against the MV F cytoplasmic tail. Both chimera replicated, as determined by end point dilutions, to reasonably high titers only about one order of magnitude lower than the titers obtained by MV. In addition, they showed the biological specificities expected: they readily infect rodent cells (which do not express a MV receptor) such as BHK (FIGS. 11, 12) where they form abundant cytoplasmic and nuclear RNPs typical for MV (FIG. 11) as well as pleomorohic particles resembling MV virions (FIG. 12) completely different from the tight shell- or cigar-like VSV virions (FIG. 13) thought to be shaped primarily by the VSV M protein.

Considering the fact that MV and VSV are only very distantly related Mononegavirales and indeed belong to different families (Paramyxoviridae and Rhabdoviridae, respectively), it seems quite likely that many different chimera involving more closely related Mononegavirales can be created and it appears not unrealistic that also chimera containing envelope proteins targeting particular cell receptors can be developed.

EXAMPLE 14

MVs Expressing Green Flourescent Protein (GFP)

To demonstrate that other genes than the CAT gene can be expressed in a recombinant vector in accordance with the present invention, the sequence encoding GFP (Chalfie et al. Science 263 (1994), 802-805) was inserted into the same position as the CAT gene in vector p(+)MPCATV, resulting in recombinant vector p(+)MPGFPV; see FIG. 10B-2.

In addition, the GFP coding sequence was inserted upstream of the N gene giving rise to recombinant vector P(+)MGFPNV (FIG. 10B-2) making sure that the rule of six was not violated and using in principle a similar gene boundary like segment as for the CAT constructs. In fact, a particularly strong expression of the GFP was achieved in this way as detected by visual evaluation of the expressed protein. It was even possible to express two foreign coding sequences at the same time in one recombinant construct as has been demonstrated with MV expressing two copies of GFP at different positions.

REFERENCES

Adams, S. M. and Blakesley, R. (1991) Linear amplification DNA sequencing. *Focus,* 13, 56-58.

Aldhous, P. (1992) Tragedy revealed in Zurich. *Nature,* 355, 577.

Andino, R., Silvera, D., Suggett, S. D., Achacoso, P. L., Miller, C. J., Baltimore, D. and Feinberg, M. B. (1994) Engineering poliovirus as a vaccine vector for the expression of diverse antigens. *Science,* 265, 1448-1451.

Ballar., I., Eschle, D., Cattaneo, R., Schmid, A., Metzler, M., Chan, J., Pifko-Hirst, S., Udem, S. A and Billeter, M. A. (1990) Infectious measles virus from cloned cDNA [retracted by Eschle D., Cattaneo R., Schmid A., Metzler M., Chan J., Pifko-Hirst S., Udem S. A, Billeter M. A. in: EMBO J., 10, 3558; 1991]. *EMBO J.,* 9, 379-384.

Baxby, D. and Paoletti, E. (1992) Potential use of non-replicating vectors as recombinant vaccines. *Vaccine,* 10, 8-9.

Billeter, M. A., Cattaneo, R., Spielhofer, P., Kaelin, K., Huber, M., Schmnid, A., Baczko, K. and ter Meulen, V. (1994) Generation and properties of measles virus mutations typically associated with subacute sclerosing panencephalitis. In Björnsson, J., Carp, R. I., Löve, A. and Wisniewski, H. M. (eds.), *Slow Infections of the Central Nervous System; the Legacy of Dr. Björn Sigurdsson*. The New York Academy of Sciences, New York, Annals of the New York Academy of Sciences Vol. 724, pp. 367-377.

Boyer, J. C. and Haenni, A. L. (1994) Infectious transcripts and cDNA clones of RNA viruses. *Virology,* 198, 415-426.

Burke, K. L., Dunn, G., Ferguson, M., Minor, P. D. and Almond, J. W. (1988) Antigen chimeras of poliovirus as potential new vaccines. *Nature,* 332, 81-82.

Calain, P. and Roux, L. (1993) The rule of six, a basic feature for efficient replication of Sendai virus defective interfering RNA. *J. Virol.,* 67, 4822-4830.

Cattaneo, R., Kaelin, K., Baczko, K. and Billeter, M. A. (1989) Measles virus editing provides an additional cysteine-rich protein. *Cell,* 56, 759-764.

Chamberlin, M. and Ryan, T. (1982) Bacteriophage DNA-dependent RNA polymerases. In Boyer, P. D. (ed.), *The Enymes* (*third edition*). Academic Press, New York, London Vol. 15, pp. 87-108.

Chomczynski, P. and Sacchi, N. (1987) Single-step method of RNA isolation by acid guanidinium thiocyanate-phenol-chloroform extraction. Anal. Biochem., 162, 156-159.

Clements, C. J. and Cutts, F. T. (1995) The epidemiology of measles: thirv years of vaccination. In ter Meulen, V. and Billeter, M. A. (eds,), *Measles Virus*. Springer GmbH & Co, Berlin, Curr. Topics in Microbiol. and Immunol. Vol. 191, pp. 13-33.

Collins, P. L., Mink, M. A., Hill, M. G., Camargo, E., Grosfeld, H. and Stec, D. S. (1993) Rescue of a 7502-nucleotide (49.3% of full-length) synthetic analog of respiratory syncytial virus genomic RNA. *Virology,* 195, 252-256.

Collins, P. L., Mink, M. A. and Stec, D. S. (1991) Rescue of synthetic analogs of respiratory syncytial virus genomic RNA and effect of truncations and mutations on the expression of a foreign reporter gene. *Proc. Natl. Acad. Sci. USA,* 88, 9663-9667.

Conzelmann, K. K. and Schnell, M. (1994) Rescue of synthetic genomic RNA analogs of rabies virus by plasmid-encoded proteins. *J. Virol.,* 68, 713-719.

Curran, J. A. and Kolakofsky, D. (1991) Rescue of a Sendai virus DI genome by other parainfluenza viruses: implications for genome replication. *Virology,* 182, 168-176.

Davanloo, P., Rosenberg, A. H., Dunn, J. J. and Studier, F. W. (1984) Cloning and expression of the gene for bacteriophage T7 RNA polymerase. *Proc. Natl. Acad. Sci. USA,* 81, 2035-2039.

Deng, H., Wang, C., Acsadi, G. and Wolff, J. A. (1991) High-efficiency protein synthesis from T7 RNA polymerase transcripts in 3T3 fibroblasts. *Gene,* 109, 193-201.

Dimock, K. and Collins. P. L. (1993) Rescue of synthetic analogs of genomic RNA and replicative-intermediate RNA of human parainfluenza virus type 3. *J. Virol.,* 67, 2772-2778.

Enami, M. and Palese, P. (1991) High-efficiency formation of influenza virus transfectants. *J. Virol.,* 65, 2711-2713.

Enders, J. F. (1962) Measles virus: historial review, isolation and behavior in various systems. *Am. J. Dis. Child.,* 103, 282-287.

Enders, J. F. and Peebles, T. C. (1954) Propagation in tissue cultures of cytopathogenic agents from patients with measles. *Proc. Soc. Exp. Biol. Med.,* 86, 277-286.

Fuerst, T. R.. Niles, E. G., Studier, F. W. and Moss, B. (1986) Eukaryotic transient-expression system based on recombinant vaccinia virus that synthesizes bacteriophage T7 RNA polymerase. *Proc. Natl. Acad. Sci. USA,* 83, 8122-8126.

Gossen, M., Bonin, A. L. and Bujard, H. (1993) Control of gene activity in higher eukaryotic cells by prokarvotic regulatory elements. *Trends Biochem. Sci.,* 18, 471-475.

Hancock, J. F.. Paterson, H. and Marshall, C. J. (1990) A polybasic domain or palmitoylation is required in addition to the CAAXS motif to localize p21ras to the plasma membrane. *Cell.* 63, 133-139.

Huber, M. (1993) *Expression of measles virus genes: Analysis of interactions between nucleocapsid protein and phosphoprotein*, Ph.D. thesis, University of Zürich, Switzerland.

Huber, M., Cattaneo, R., Spielhofer, P., Oervell, C., Norrby, E., Messerli, M., Perriard, J. C. and Billeter, M. A. (1991) Measles virus phosphoprotein retains the nucleocapsid protein in the cytoplasm. *Virology,* 185, 299-308.

Iverson, L. E. and Rose, J. K. (1981) Localized attenuation and discontinuous synthesis during vesicular stomatitis virus transcription. *Cell,* 23, 477-484.

Kaelin, K. (1989) *RNA editing in the measles virus phosphoprotein gene provides an additional protein*, Diploma thesis, University of Zürich, Switzerland.

Lawson, N., Stillman, E. A., Whitt, M. A. and Rose, J. K. (1995) Recombinant vesicular stomatitis viruses from DNA. *Proc. Natl. Acad. Sci. USA,* 92, 4477-4481.

Luytjes, W., Krystal, M., Enami, M., Parvin, J. D. and Palese, P. (1989) Amplification, expression, and packaging of a foreign gene by influenza virus. *Cell,* 59, 1107-1113.

Mindich, L. (1995) Heterologous recombination in the segmented dsRNA genome of bacteriophage f6. *Seminars in Virology,* 6, 75-83.

Moss, B., Elroy-Stein, O., Mizukami, T., Alexander, W. A. and Fuerst, T. R. (1990) Product review. New mammalian expression vectors. *Nature,* 348, 91-92.

Naniche, D., Varior-Krishnan, G., Cervoni, F., Wild, T. F., Rossi, B., Rabourdin-Combe, C. and Gerlier, D. (1993) Human membrane cofactor protein (CD46) acts as C a cellular receptor for measles virus. *J. Virol.,* 67, 6025-6032.

Norrby, E. (1995) The paradigms of measles vaccinology. In ter Meulen, V. and Billeter, M. A. (eds.), Measles virus. Springer GmbH & Co., Berlin, Current Topics in Microbiol. and Immunol. Vol. 191, pp. 167-180.

Oervell, C. and Norrby, E. (1980) Immunological relationships between homologous structural polypeptides of measles and canine distemper virus. *J. Gen. Virol.,* 50, 231-245.

Park, K. H., Huang, T., Correia, F. F. and Krystal, M. (1991) Rescue of a foreign gene by Sendai virus. *Proc. Natl. Acad. Sci. USA,* 88, 5537-5541.

Pattnaik, A. K. and Wertz, G. W. (1990) Replication and amplification of defective interfering particle RNAs of vesicular stomatitis virus in cells expressing viral proteins from vectors containing cloned cDNAs. *J. Virol.,* 64, 2948-2957.

Pelletier, J. and Sonenberg, N. (1988) Internal initiation of translation of eukaryotic MRNA directed by a sequence derived from poliovirus RNA. *Nature,* 334, 320-325.

Perrotta, A. T. and Been, M. D. (1990) The self-cleaving domain from the genomic RNA of hepatitis delta virus: sequence requirements and the effects of denaturants. *Nucleic Acids Res.,* 18, 6821-6827.

Pringle, C. R. (1991) The *Mononegavirales*. In Francki, R. I. B., Fauquet, C. M., Knudson, D. L. and Brown, F. (eds.), *Classification and Nomenclature of Viruses*. Springer-Verlag, Wien N.Y., pp. 239-262.

Racaniello, V. R. and Baltimore, D. (1981) Cloned poliovirus cDNA is infectious in mammalian cells. *Science,* 214, 916-919.

Radecke, F. and Billeter, M. A. (1995) Appendix: measles virus antigenome and protein consensus sequences. In ter Meulen, V. and Billeter, M. A. (eds.), *Measles Virus*. Springer GmbH & Co., Berlin, Current Topics in Microbiology and Immunology Vol. 191, pp. 181-192.

Re, G. G. (1991) Deletion mutants of paramyxoviruses. In Kingsbury, D. W. (ed.), *The Paramyxoviruses*. Plenum Press, New York, The Viruses, pp. 275-298.

Rice, C. M., Levis, R., Strauss, J. H. and Huang, H. V. (1987) Infectious transcripts from Sindbis virus cDNA clones. *J. Virol.,* 61, 3809-3819.

Rozenblatt, S., Koch, T., Pinhasi, O. and Bratosin, S. (1979) Infective substructures of measles virus from acutely and persistently infected cells. *J. Virol.,* 32, 329-333.

Schnell, M. J., Mebatsion, T. and Conzelmann, K. K. (1994) Infectious rabies viruses from cloned cDNA. *EMBO J.,* 13, 4195-4203.

Schubert, M., Harmison, G. G., Richardson, C. D. and Meier, E. (1985) Expression of a cDNA encoding a functional 241 kD VSV RNA polymerase. *Proc. Natl. Acad. Sci. USA,* 82, 7984-7988.

Severne, Y., Wieland, S., Schaffner, W., and Rusconi, S. (1988). Metal binding "finger" structures in the glucocorticoid receptor defined by site-directed mutagenesis. EMBO J. 7,2503-2508.

Sheshberadaran, H., Chen, S. N. and Norrby, E. (1983) Monoclonal antibodies against five structural components of measles virus. *Virology,* 128, 341-353.

Sidhu, M. S., Chan, J., Kaelin, K., Spielhofer, P., Radecke, F., Schneider, H., Masurekar, M., Dowling, P. C., Billeter, M. A. and Udem, S. A (1995) Rescue of synthetic measles virus minireplicons: measles genomic termini direct efficient expression and propagation of a reporter gene. *Virology,* 208, 795-799.

Sjoberg, E. M., Suomalainen, M. and Garoff, H. (1994) A Significantly Improved Semliki Forest Virus Expression System Based On Translation Enhancer Segments From the Viral Capsid Gene. *Bio-Technology,* 12, 1127-1131.

Skerra, A. (1992) Phosphorothioate primers improve the amplification of DNA sequences by DNA polymerases with proofreading activity. *Nucleic Acids Res.,* 20, 3551-3554.

Soriano, P., Montgomery, C., Geske, R. and Bradley, A. (1991) Targeted disruption of the c-src proto-oncogene leads to osteopetrosis in mice. *Cell,* 64, 693-702.

Spehner, D., Kirn, A. and Drillien, R. (1991) Assembly of nucleocapsidlike structures in animal cells infected with a vaccinia virus recombinant encoding the measles virus nucleoprotein. *J. Virol.,* 65, 6296-6300.

Sutter, G. and Moss, B. (1992) Nonreplicating vaccinia vector efficiently expresses recombinant genes. *Proc. Natl. Acad. Sci. USA,* 89, 10847-10851.

Taniguchi, T., Palmieri, M. and Weissmann, C. (1978) Qb DNA-containing hybrid plasmids giving rise to Qb phage formation in the bacterial host. *Nature,* 274, 2293-2298.

Wertz, G. W., Whelan, S., LeGrone, A. and Ball, L. A. (1994) Extent of terminal complementariry modulates the balance between transcription and replication of vesicular stomatitis virus RNA. *Proc. Natl. Acad. Sci. USA,* 91, 8587-8591.

Willenbrink, W. and Neubert, W. N. (1994) Long-term replication of Sendai virus defective interfering particle nucleocapsids in stable helper cell lines. *J. Virol.,* 68, 8413-8417.

Xiong, C., Levis, R., Shen, P., Schlesinger, S., Rice, C. M. and Huang, H. V. (1989) Sindbis virus: an efficient, broad range vector for gene expression in animal cells. *Science,* 243, 1188-1191.

The invention claimed is:

1. An isolated eukaryotic host cell comprising (1) stably transfected expression plasmids that allow genomic expression of an exogenous RNA polymerase, a viral N protein, and a viral P protein in the host cell; (2) a nucleic acid sequence encoding a viral L protein; and (3) a cDNA molecule, said cDNA molecule comprising:

(a) a (+) strand sequence of a non-segmented negative-strand RNA virus of the family Paramyxoviridae from which RNA transcripts bearing the authentic 3' termini can be transcribed; and (b) an expression control sequence, wherein said (+) strand sequence of a non-segmented negative-strand RNA virus is operatively linked to the expression control sequence, and wherein the host cell, without a replicating vaccinia helper virus, produces an infectious RNA virus containing the (−) strand sequence of the non-segmented negative-strand RNA virus of the family Paramyxoviridae, said (−) strand sequence of the non-segmented negative-strand RNA virus obeying the rule of six.

2. The host cell of claim 1, wherein the nucleic acid encoding the viral L protein is stably transfected into the host cell, said stable transfection allowing genomic expression of the viral L protein in the host cell.

3. The host cell of claim 1, wherein the nucleic acid sequence encoding the viral L protein is derived from measles or mumps virus, and wherein the viral N and P proteins are encoded by nucleic acid sequences derived from measles or mumps virus.

4. The host cell of claim 3, wherein the non-segmented negative-strand RNA virus is measles virus.

5. The host cell of claim 3, wherein the non-segmented negative-strand RNA virus is mumps virus.

6. The host cell of claim 1, wherein the expression control sequence comprises an RNA polymerase promoter.

7. The host cell of claim 6, wherein the RNA polymerase promoter is a heterologous RNA polymerase promoter, with respect to the non-segmented negative-strand RNA virus.

8. The host cell of claim 1, wherein the (+) strand sequence of the non-segmented negative-strand RNA virus contains a sequence variation, with respect to a wild-type non-segmented negative-strand RNA virus.

9. The host cell of claim 8, wherein the sequence variation is a deletion.

10. The host cell of claim 1, further comprising an expressible DNA fragment inserted into said (+) strand sequence of a non-segmented negative-strand RNA virus.

11. The host cell of claim 10, wherein the expressible DNA fragment is inserted into a non-coding region of said (+) strand sequence of a non-segmented negative-strand RNA virus.

12. The host cell of claim 11, wherein the expressible DNA fragment is inserted in the 5' terminal region of the (+) strand sequence of a non-segmented negative-strand RNA virus.

13. The host cell of claim 12, wherein said expressible DNA fragment is homologous or heterologous with respect to the non-segmented negative-strand RNA virus.

14. The host cell of claim 13, wherein the expressible DNA fragment encodes at least one immunogenic epitope.

15. The host cell of claim 14, wherein said expressible DNA fragment encodes an immunogenic epitope of an envelope protein of a pathogen.

16. The host cell of claim 10, wherein said expressible DNA fragment is derived from a virus, a bacterium, a pathogen, or a parasite.

17. The host cell of claim 10, wherein said expressible DNA fragment encodes a toxin.

18. The host cell of claim 10 wherein the expressible DNA fragment is inserted into a region of said (+) strand sequence encoding a viral protein, said insertion being effected in a manner maintaining the reading frame to create a fusion protein, and permitting the expression of said fragment under the control of the promoter of the viral protein.

19. The host cell of claim 18 wherein the expressible fragment encodes an immunogenic epitope.

20. The host cell of claim 10, wherein the expressible DNA fragment is inserted upstream of a viral protein coding region to avoid formation of a fusion protein, but allowing expression of the downstream viral protein coding region either by a stop/restart mechanism where the last A residue of the upstream termination triplet coincides with that of the start codon of the downstream coding region, or by placing an internal ribosome entry site (IRES) between the two coding regions.

* * * * *

SEQUENCE LISTING

<160> NUMBER OF SEQ ID NOS: 16

<210> SEQ ID NO 1
<211> LENGTH: 82
<212> TYPE: DNA
<213> ORGANISM: Homosapien

<400> SEQUENCE: 1
ctagcctacc ctccatcatt gttataaaaa acttaggaac caggtccaca cagccgccag    60
cccatcaacg cgtatcgcga ta                                            82

<210> SEQ ID NO 2
<211> LENGTH: 38
<212> TYPE: DNA
<213> ORGANISM: Homosapien

<400> SEQUENCE: 2
ggggaaccat cgatggataa gaatgcggcc gcaggtac                           38

<210> SEQ ID NO 3
<211> LENGTH: 36
<212> TYPE: DNA
<213> ORGANISM: Homosapien

<400> SEQUENCE: 3
ctgcggccgc attcttatcc atcgatggtt ccccgc                             36

<210> SEQ ID NO 4
<211> LENGTH: 25
<212> TYPE: DNA
<213> ORGANISM: Homosapien

<400> SEQUENCE: 4
accaaacaaa gttgggtaag gatag                                         25

<210> SEQ ID NO 5
<211> LENGTH: 22
<212> TYPE: DNA
<213> ORGANISM: Homosapien

<400> SEQUENCE: 5
cagcgtcgtc atcgctctct cc                                            22

<210> SEQ ID NO 6
<211> LENGTH: 24
<212> TYPE: DNA
<213> ORGANISM: Homosapien

<400> SEQUENCE: 6
gagaagctag aggaattggc agcc                                          24

<210> SEQ ID NO 7
<211> LENGTH: 28
<212> TYPE: DNA
<213> ORGANISM: Homosapien

<400> SEQUENCE: 7
ttctgaagac tcaccagaca aagctggg                                      28

<210> SEQ ID NO 8
<211> LENGTH: 35
<212> TYPE: DNA
<213> ORGANISM: Homosapien

<400> SEQUENCE: 8
ataagaatgc ggccgcatcc ggatatagtt cctcc                              35

<210> SEQ ID NO 9
<211> LENGTH: 33
<212> TYPE: DNA
<213> ORGANISM: Homosapien

<400> SEQUENCE: 9
ttctgaagac tctggtggcc ggcatggtcc cag                                    33

<210> SEQ ID NO 10
<211> LENGTH: 32
<212> TYPE: DNA
<213> ORGANISM: Homosapien

<400> SEQUENCE: 10
ccgaatcaag actcatccaa tgtccatcat gg                                     32

<210> SEQ ID NO 11
<211> LENGTH: 28
<212> TYPE: DNA
<213> ORGANISM: Homosapien

<400> SEQUENCE: 11
agagagattg ccccaatgga tttgaccg                                          28

<210> SEQ ID NO 12
<211> LENGTH: 30
<212> TYPE: DNA
<213> ORGANISM: Homosapien

<400> SEQUENCE: 12
gtggatccat ggactcgcta tctgtcaacc                                        30

<210> SEQ ID NO 13
<211> LENGTH: 29
<212> TYPE: DNA
<213> ORGANISM: Homosapien

<400> SEQUENCE: 13
agttagtgtc ccttaagcat tggaaaacc                                         29

<210> SEQ ID NO 14
<211> LENGTH: 29
<212> TYPE: DNA
<213> ORGANISM: Homosapien

<400> SEQUENCE: 14
actcggtatc actgccgagg atgcaaggc                                         29

<210> SEQ ID NO 15
<211> LENGTH: 36
<212> TYPE: DNA
<213> ORGANISM: Homosapien

<400> SEQUENCE: 15
ctagcctacc ctccatcatt gttataaaaa acttag                                 36

<210> SEQ ID NO 16
<211> LENGTH: 23
<212> TYPE: DNA
<213> ORGANISM: Homosapien

<400> SEQUENCE: 16
ccggttataa caatgatgga ggg                                               23